(12) United States Patent
Shih

(10) Patent No.: US 12,030,166 B2
(45) Date of Patent: Jul. 9, 2024

(54) FORCE-LIMITING AND DAMPING DEVICE

(71) Applicant: Jui-Yuan Shih, Changhua County (TW)

(72) Inventor: Jui-Yuan Shih, Changhua County (TW)

( * ) Notice: Subject to any disclaimer, the term of this patent is extended or adjusted under 35 U.S.C. 154(b) by 690 days.

(21) Appl. No.: 17/007,537

(22) Filed: Aug. 31, 2020

(65) Prior Publication Data

US 2021/0086336 A1 Mar. 25, 2021

(30) Foreign Application Priority Data

Sep. 20, 2019 (TW) ................................ 108134075

(51) Int. Cl.
*B25D 1/12* (2006.01)

(52) U.S. Cl.
CPC .......... *B25D 1/12* (2013.01); *B25D 2250/005* (2013.01); *B25D 2250/085* (2013.01); *B25D 2250/371* (2013.01)

(58) Field of Classification Search
CPC .............. B25D 1/12; B25D 2250/005; B25D 2250/085; B25D 2250/371; B25D 1/00; B25D 1/06; B25D 1/08; B25D 17/24; B25D 2250/195; B25D 2222/57; B26B 23/00; B25G 1/01; B25G 1/02; A61F 2002/4681; A61B 17/92; A61B 2017/922; A61C 3/08; A61C 8/0089; A63B 53/0416; A63B 60/54
USPC ............................................................ 81/22
See application file for complete search history.

(56) References Cited

U.S. PATENT DOCUMENTS

| 5,282,805 A | * | 2/1994 | Richelsoph | A61F 2/4607 |
| | | | | 606/100 |
| 9,982,733 B2 | * | 5/2018 | Shih | B25D 1/02 |
| 2017/0211646 A1 | * | 7/2017 | Shih | B25G 1/102 |

FOREIGN PATENT DOCUMENTS

| CN | 108743313 | * | 11/2018 |
| DE | 408541 A | * | 2/1966 |
| KR | 20100050116 | * | 5/2010 |

* cited by examiner

*Primary Examiner* — Robert J Scruggs
(74) *Attorney, Agent, or Firm* — Rosenberg, Klein & Lee

(57) ABSTRACT

A force-limiting and damping device has a body, a tapping element, a shock-absorbing element, and a limiting module. The body has a connecting segment and a holding segment. The tapping element is connected to the body to move relative to the connecting segment and has a mounting segment, a tapping segment, and a fixing segment. The mounting segment is movably connected to the connecting segment. The tapping segment is disposed on an end of the mounting segment below the connecting segment. The fixing segment is connected to the mounting segment and abuts the connecting segment. The shock-absorbing element is mounted on the mounting segment and abuts the connecting segment and the tapping segment. The limiting module is mounted between the body and the tapping element and has a force-limiting element mounted between the mounting segment and the connecting segment to provide a force-limiting reminder effect and a damping effect.

33 Claims, 18 Drawing Sheets

FORCE-LIMITING AND DAMPING DEVICE

BACKGROUND OF THE INVENTION

1. Field of the Invention

The present invention relates to a force-limiting and damping device, and more particularly to a force-limiting and damping device that may provide a reminder effect to a user, may improve feel of vibration, and may adjust force range according to the user's need.

2. Description of Related Art

A conventional hammer or mallet in the industry is used to tap nails in wood, cement walls or metal plates. During the tapping process, the conventional hammer or mallet may be bounced by a reaction force, and this will shorten the contacting time of the conventional hammer or mallet with the nails, and will tend to make the nails bent or deflect. Furthermore, the instant rebound reaction force will be converted into heat and noise as energy dissipation, and this will reduce the tapping efficiency of the user. That is, the applied force that is provided by the user is not tapped on the nails sufficiently, and the user needs to tap the nails repeatedly to enable the nails to knock and fix in wooden or metal plates, and this will increase the number and time of tapping the nails. In addition, when the user holds a handle of the conventional hammer or mallet, the vibration generated during the bouncing process also makes the user feel uncomfortable. Additionally, a conventional medical or surgical hammer has a similar structure as the industrial hammer, and the tapping face of the conventional surgical or surgery hammer is mostly a rigid structure. Therefore, when dentists use the conventional medical or surgical hammer in a dental surgery, the returning vibration generated by the reaction force will make the dentists feel uncomfortable and difficult to firmly hold the conventional medical or surgery hammer, and the patient will feel pain due to the tapping force and may even have a concussion.

According to the above-mentioned description, since in use of each one of the conventional industrial hammer or mallet and the conventional medical or surgical hammer, an instant rebound reaction force may be generated by the rigid tapping face or tapping head, and noise and discomfort are also generated during the tapping process, and this will affect the smoothness and control of operation. Furthermore, each one of the conventional industrial hammer or mallet and the conventional medical or surgical hammer cannot provide a reminder effect of strength to the user, and it is impossible for users to tap and use within the corresponding range of force. Consequently, it is easy for the shock caused by the reaction force to make the user unable to hold the hammer/mallet steadily and feel uncomfortable, and it will make the stressed object feel vibration or discomfort. Additionally, the conventional industrial hammer, hammer, medical hammer or surgical hammer, etc., cannot be adjusted according to the needs of the user, and their practicality and flexibility are relatively limited.

To overcome the shortcomings, the present invention tends to provide a force-limiting and damping device to mitigate the aforementioned problems.

SUMMARY OF THE INVENTION

The main objective of the invention is to provide a force-limiting and damping device that may provide a reminder effect to a user, may improve feel of vibration, and may adjust force range according to the user's need.

A force-limiting and damping device in accordance with the present invention has a body, a tapping element, a shock-absorbing element, and a limiting module. The body has a connecting segment and a holding segment. The tapping element is connected to the body to move relative to the connecting segment and has a mounting segment, a tapping segment, and a fixing segment. The mounting segment is movably connected to the connecting segment. The tapping segment is disposed on an end of the mounting segment below the connecting segment. The fixing segment is connected to the mounting segment and abuts the connecting segment. The shock-absorbing element is mounted on the mounting segment and abuts the connecting segment and the tapping segment. The limiting module is mounted between the body and the tapping element and has a force-limiting element mounted between the mounting segment and the connecting segment to provide a force-limiting reminder effect and a damping effect.

Other objects, advantages and novel features of the invention will become more apparent from the following detailed description when taken in conjunction with the accompanying drawings.

DETAILED DESCRIPTION OF PREFERRED EMBODIMENTS

Figure 1:
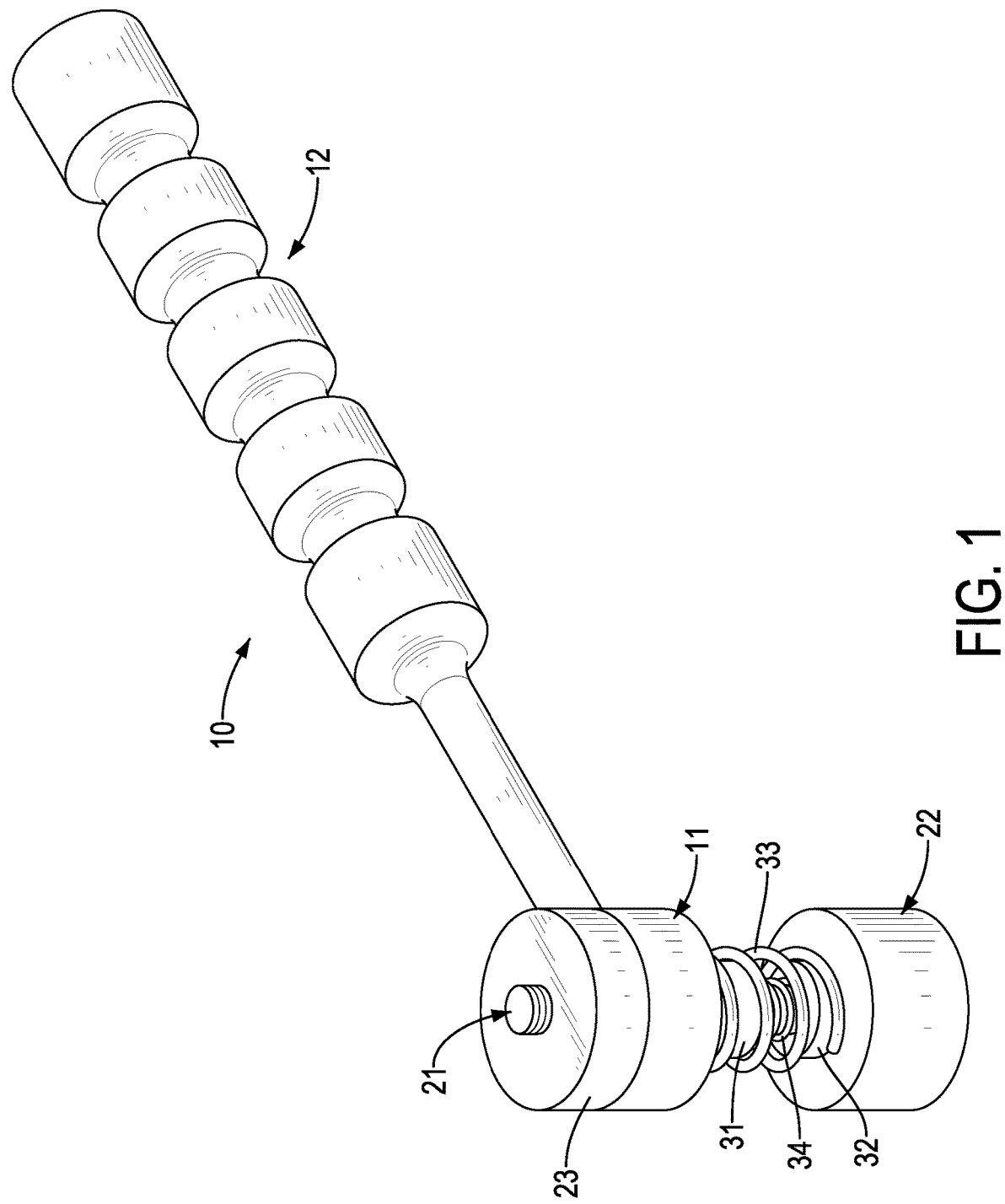
FIG. 1 is a perspective view of a first embodiment of a force-limiting and damping device in accordance with the present invention.
Figure 2:
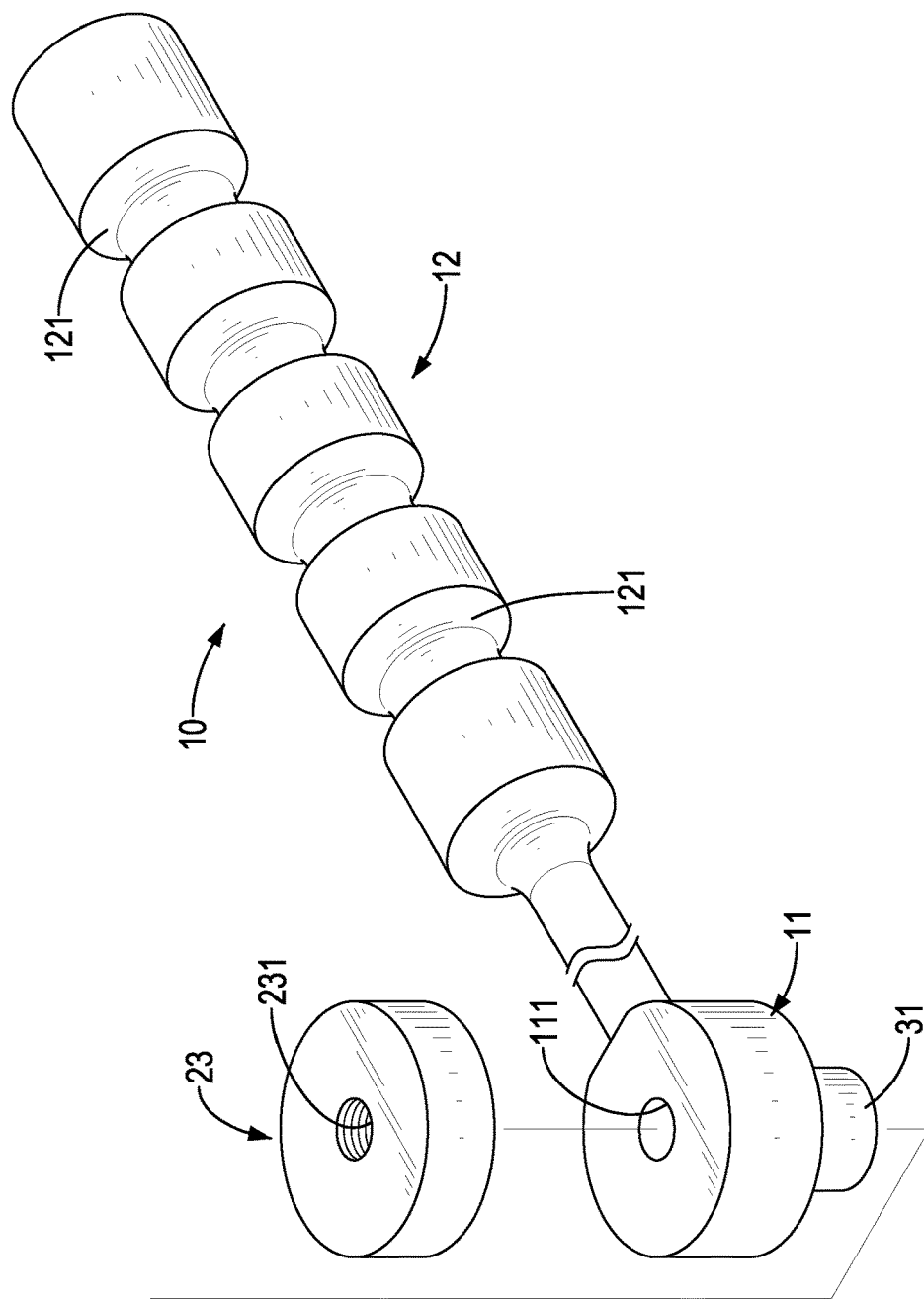
FIG. 2 is an exploded perspective view of the force-limiting and damping device in FIG. 1.
Figure 3:
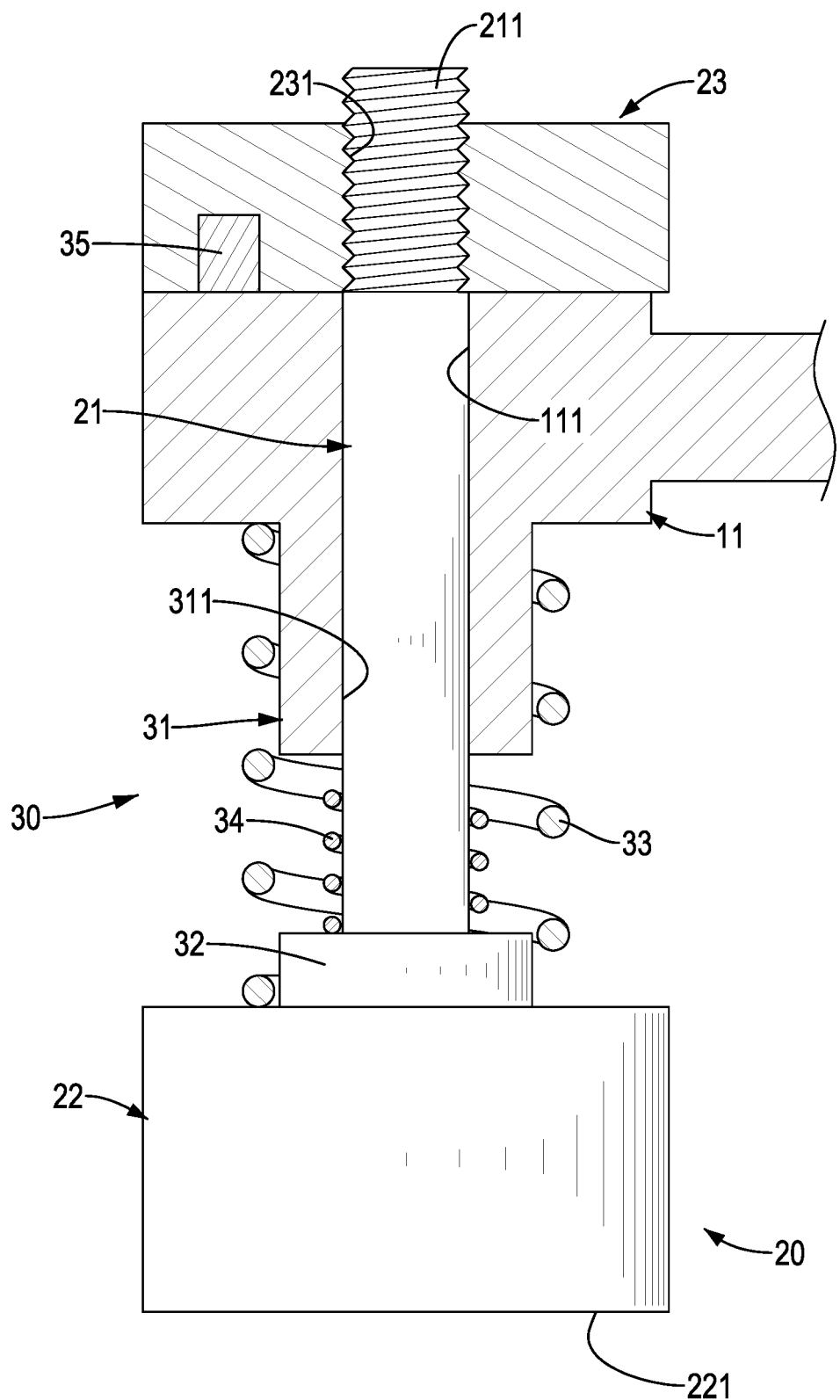
FIG. 3 is an enlarged cross sectional side view of the force-limiting and damping device in FIG. 1.

With reference to FIGS. 1 to 3, a first embodiment of a force-limiting and damping device in accordance with the present invention comprises a body 10, a tapping element 20, and a limiting module 30.

The body 10 may be an elongated metal shaft, and has a front end, a rear end, a connecting segment 11, and a holding segment 12. The connecting segment 11 is formed on and protrudes from the front end of the body 10, and has a top side, a bottom side, an external surface, and a mounting hole 111. The mounting hole 111 is axially formed through the top side and the bottom side of the connecting segment 11. The holding segment 12 is formed on the rear end of the body 10, is opposite the connecting segment 11, and has an external surface and a skidproof structure. The skidproof structure is disposed on the external surface of the holding segment 12. Additionally, the skidproof structure has multiple annular grooves 121 formed in the external surface of the holding segment 12 at spaced intervals to enable a user to hold the holding segment 12 of the body 10 firmly.

The tapping element 20 is connected to the body 10 to move relative to the connecting segment 11, and has a mounting segment 21, a tapping segment 22, and a fixing segment 23. The mounting segment 21 is movably connected to the connecting segment 11 of the body 10. Furthermore, the mounting segment 21 is a rod that extends through the mounting hole 111 of the connecting segment 11. Additionally, the mounting segment 21 has a cross section corresponding to a cross section of the mounting hole 111. When the cross section of the mounting segment 21 is round, the mounting segment 21 may be rotated relative to the connecting segment 11. Furthermore, when the cross section of the mounting segment 21 is polygonal, the mounting segment 21 only can move relative to the connecting segment 11 without rotating. The mounting segment 21 has an external surface, a holding end, a forming end, and a locking structure 211. The holding end of the mounting segment 21 extends out of the top side of the connecting segment 11 via the mounting hole 111. The forming end of the mounting segment 21 extends out of the bottom side of the connecting segment 11 via the mounting hole 111. The locking structure 211 may be an outer screw, and is disposed on the external surface of the mounting segment 21 adjacent to the holding end of the mounting segment 21.

The tapping segment 22 is disposed on the forming end of the mounting segment 21, is opposite the locking structure 211, and is mounted below the connecting segment 11. Additionally, the tapping segment 22 is integrally formed with the mounting segment 21, and may be made of metal, polyethylene (PE), hard material such as plastic, or elastic materials such as rubber, silicone or wood. Furthermore, the tapping segment 22 may be made of magnetic metal to enable the tapping segment 22 to attract a nail in use. The tapping segment 22 may be a spheroid or may be flat, axe-like, curved or tapered. Additionally, the tapping segment 22 has a tapping face 221 disposed on a bottom of the tapping segment 22, and the tapping face 221 may be made of metal, polyethylene (PE), hard material such as plastic, or elastic materials such as rubber, silicone, wood or leather.

The fixing segment 23 is connected to the mounting segment 21 and abuts the connecting segment 11 of the body 10 to hold the tapping segment 22 below the connecting segment 11. The structural relationship between the fixing segment 23 and the mounting segment 21 is an adjustable structure. Further, the fixing segment 23 is disc-shaped and has a top side, a bottom side, and a fixing hole 231. The fixing hole 231 is formed through the top side and the bottom side of the fixing segment 23, aligns with the mounting hole 111 of the connecting segment 11, and is connected to the locking structure 211 of the mounting segment 21. Furthermore, the fixing hole 231 has an inner thread screwed with the outer screw of the locking structure 211. With reference to FIG. 3, a connecting position between the fixing segment 23 and the mounting segment 21 can be adjusted, so as to change a distance between the tapping segment 22 and the connecting segment 11.

The limiting module 30 is mounted on the mounting segment 21 of the tapping element 20, and abuts against the connecting segment 11 of the body 10 and the tapping segment 22 of the tapping element 20. The limiting module 30 is used to remind a user whether the tapping force exceeds the set force range of the force-limiting and damping device when tapping. The limiting module 30 has a sleeve element 31, a positioning seat 32, a shock-absorbing element 33, and a force-limiting element 34. The sleeve element 31 is formed on and protrudes from the bottom side of the connecting segment 11 and has a through hole 311 formed through the sleeve element 31 and communicating with the mounting hole 111 of the connecting segment 11. The sleeve element 31 has an outer diameter smaller than an outer diameter of the connecting segment 11, and a first stepped face is formed at a connecting position between the sleeve element 31 and the connecting segment 11.

The positioning seat 32 is formed on a connecting position between the mounting segment 21 and the tapping segment 22, and has an outer diameter smaller than an outer diameter of the tapping segment 22 and larger than an outer diameter of the mounting segment 21, and two second stepped faces are respectively formed at a connecting position between the mounting segment 21 and the positioning seat 32 and a connecting position between the positioning seat 32 and the tapping segment 22. Furthermore, the sleeve element 31 is disposed above the positioning seat 32 at a spaced interval. The shock-absorbing element 33 is mounted on the sleeve element 31 and the positioning seat 32, and abuts against the connecting segment 11 and the tapping segment 22. The force-limiting element 34 is mounted on the mounting segment 21 between the sleeve element 31 and the positioning seat 32. When the connecting position between the fixing segment 23 and the mounting segment 21 is adjusted, the compression or expansion state of the shock-absorbing element 33 between the tapping segment 22 and the connecting segment 11 can be adjusted.

Additionally, the shock-absorbing element 33 may be a spring, and the spring may have a uniform inner diameter (the inner diameter is the same at a top end and a bottom end of the spring) or have different inner diameters (the inner diameter at the top end of the spring is wider than the inner diameter at the bottom end of the spring). When using a spring with a uniform inner diameter as the shock-absorbing element 33, portions of the spring may be knocked against each other during a tapping process of the force-limiting and damping device. When using a spring with different inner diameters as the shock-absorbing element 33, portions of the spring may not be knocked against each other during a tapping process of the force-limiting and damping device.

Further, the shock-absorbing element 33 may be made of flexible material in a fixed shape such as a spring, rubber, silicone, a metal washer, flexible metal block or flexible block. Furthermore, the spring may be mounted in the rubber or the silicone to form the shock-absorbing element 33. Additionally, in use, different elastic forces of the shock-absorbing elements 33 can be selected, and the shock-absorbing element 33 can be pre-compressed to set the compression force (such as 5, 10 or 15 kilograms, etc.) of the shock-absorbing element 33 by the fixing segment 23. In use, when the tapping force is smaller than a preset compression force of the shock-absorbing element 33, the user may feel the tapping segment 22 generating an instant rebound, and when the tapping force is larger than the preset compression force of the shock-absorbing element 33, the user may feel the tapping segment 22 generating a delayed rebound. Therefore, the user can be reminded of the tapping force by identifying the compressed extent, and this may provide a force-limiting reminder effect to the user.

With reference to FIG. 3, the limiting module 30 further has at least one magnetic member 35, and the at least one magnetic member 35 is disposed on the fixing segment 23 to attract the connecting segment 11 by a magnetic attracting force between the at least one magnetic member 35 and the connecting segment 11, and this may provide a force-limiting reminder effect to the user.

The force-limiting element 34 may be made of flexible material in a fixed shape such as a spring, annular rubber, a silicone block, a flexible metal block or a flexible block, and the spring may be mounted in the rubber or the silicone to form the force-limiting element 34. Furthermore, the force-limiting element 34 may be slidably mounted on the mounting segment 21 or may be fixed on the mounting segment 21. In addition, the force-limiting element 34 is fixed on the positioning seat 32 and is disposed below the sleeve element 31 at a spaced interval, or the force-limiting element 34 is fixed on the sleeve element 31 and is disposed above the positioning seat 32 at a spaced interval. Furthermore, the limiting module 30 has a reminder element disposed on the force-limiting element 34 to emit light or sound for reminding the user when the sleeve element 31 contacts the force-limiting element 34.

Figure 4:
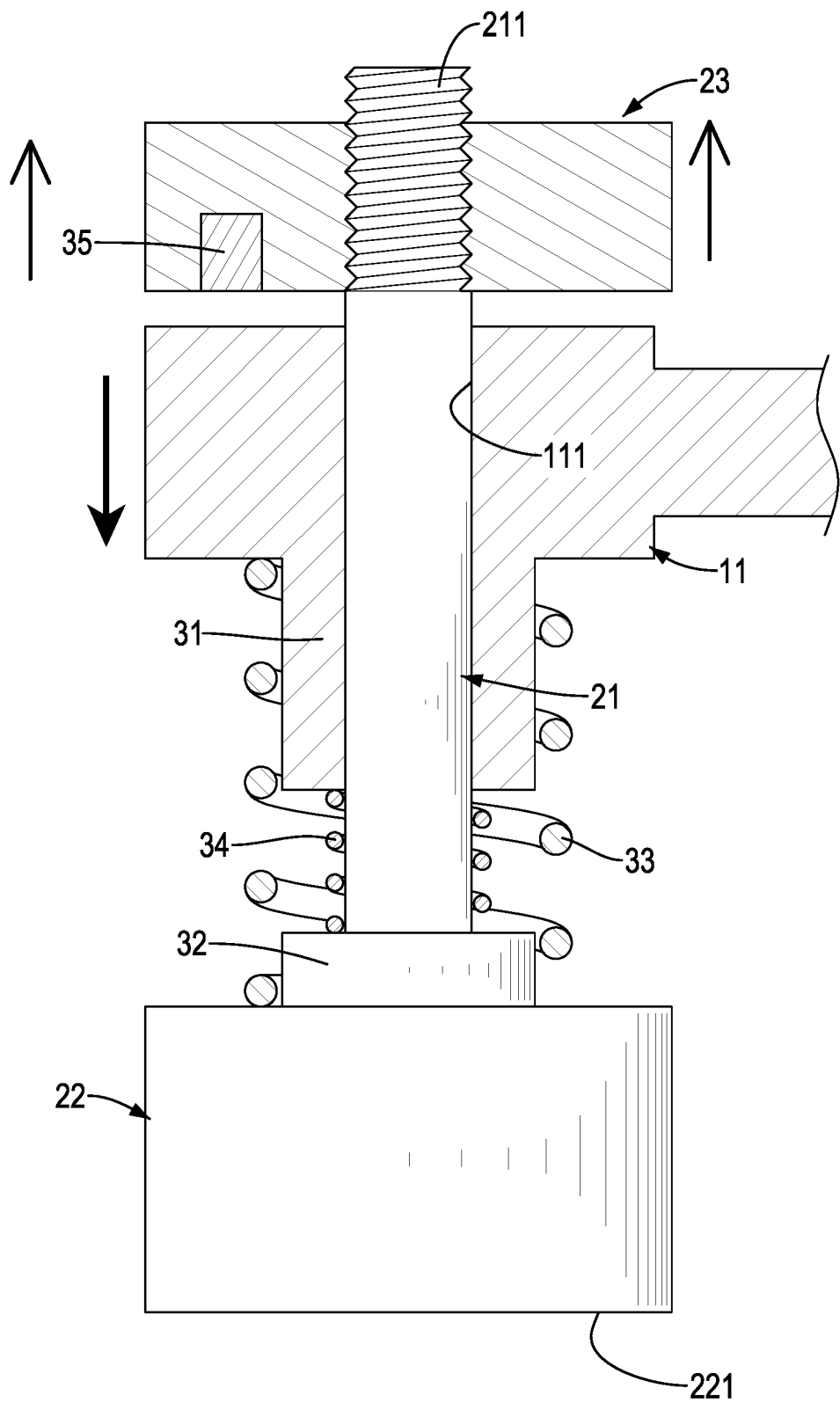
FIGS. 4 and 5 are enlarged and operational side views in partial sections of the force-limiting and damping device in FIG. 1.

According to the above-mentioned structural relationship and features of the first embodiment of a force-limiting and damping device in accordance with the present invention, the force-limiting and damping device may be a medical hammer to tap a dental implant into a patient's jaw bones or an industrial hammer to tap a nail into a wooden board. With reference to FIG. 1, the user holds and moves the holding segment 12 of the body 10 to enable the tapping segment 22 of the tapping element 20 to hit against the nail or the dental implant. With further reference to FIG. 4, a reaction force is generated when the tapping segment 22 knocks against the nail or the dental implant. When the reaction force is smaller than the magnetic attracting force between the at least one magnetic member 35 and the connecting segment 11 and the preset compression force of the shock-absorbing element 33, the fixing segment 23 will not be separated from the connecting segment 11 along with the mounting segment 21, the sleeve element 31 does not compress the shock-absorbing element 33, and the tapping face 221 of the tapping segment 22 will not move relative to the connecting segment 11, and the tapping segment 22 will receive an instant rebound reaction force.

Figure 5:
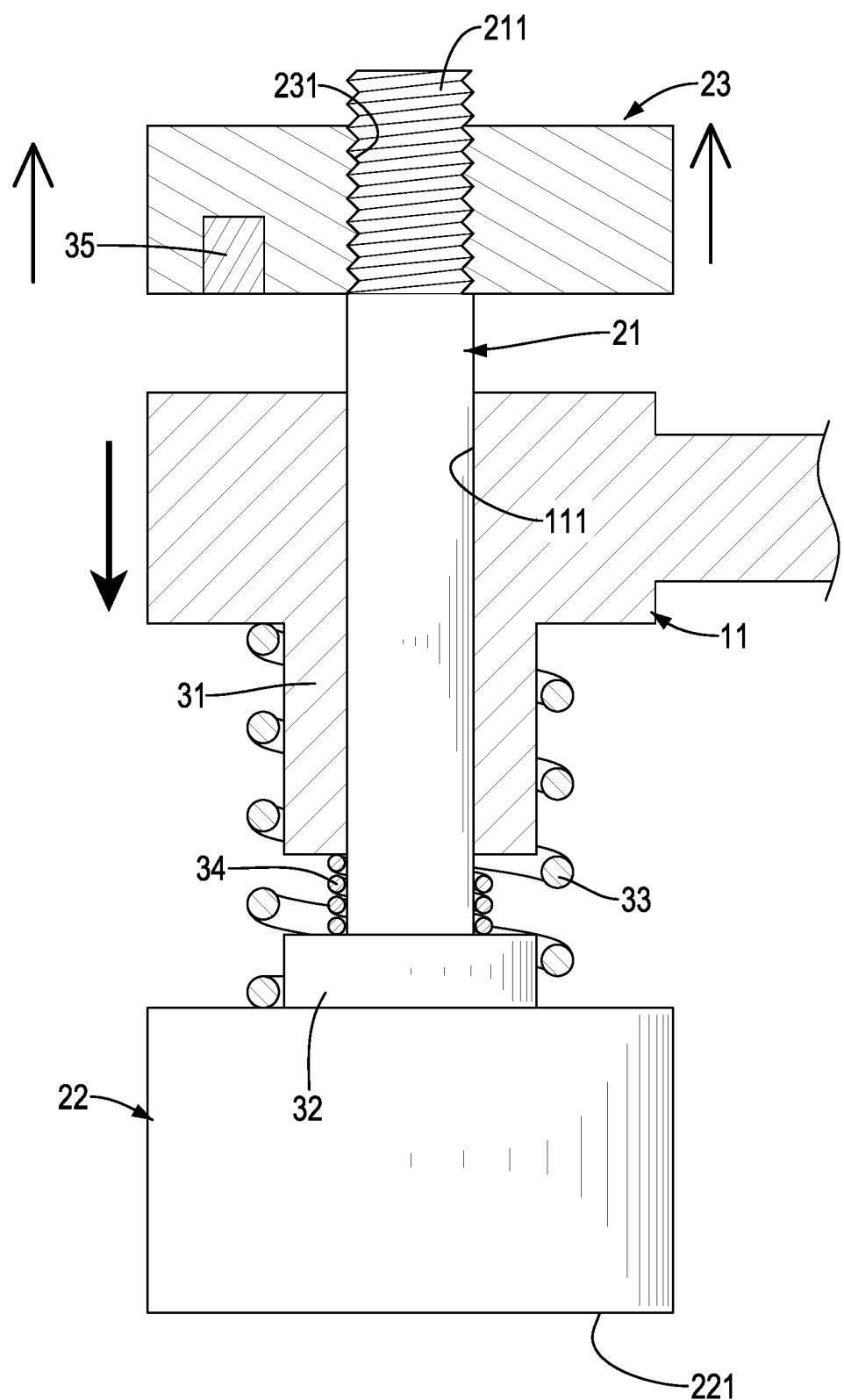

Furthermore, with reference to FIG. 4, when the user applies a larger force to tap the nail or the dental implant, the reaction force is larger than the magnetic attracting force between the at least one magnetic member 35 and the connecting segment 11 and the preset compression force of the shock-absorbing element 33, the tapping segment 20 will move upwardly relative to the connecting segment 11 to separate the fixing segment 23 from the connecting segment 11 along with the mounting segment 21 and to compress the shock-absorbing element 33. Then, the tapping energy is transformed into the compressed potential energy of the shock-absorbing element 33. With reference to FIG. 5, the body 10 will be moved toward the nail or the dental implant with the waving direction of the user (not going to rebound). When the sleeve element 31 is moved with the body 10 to compress the force-limiting element 34, the tapping face 221 of the tapping segment 22 will not move relative to the connecting segment 11 by the compressed force-limiting element 34, and the tapping segment 22 will receive an instant rebound reaction force.

By the way of mounting the limiting module 30 between the connecting segment 11 and the tapping segment 22, a delayed rebound and damping effect is generated to the reaction force to prevent the industrial hammer from bouncing during the tapping process by an instant rebound reaction force. Then, the nail will not bend or deflect easily, and the user's applied force is continuously transferred to the nail, and this may reduce noise and the loss of energy. Furthermore, the user may only need to tap the nail into the wooden board several times, and this may reduce the number and time of tapping the nail into the wooden board. Furthermore, when the force-limiting and damping device is a medical hammer, in use, the damping effect that is provided by the limiting module 30 may reduce the uncomfortable feel of the user and the pain of the patient, and the user may hold the body 10 firmly to tap. Furthermore, the limiting module 30 can provide not only damping and shock-absorbing effects, but also a force-applying reminder effect via the force-limiting element 34.

Additionally, with reference to FIG. 2, the user may rotate the fixing segment 23 to separate from the mounting segment 21, and mount the limiting module 30 (including the shock-absorbing element 33 and the force-limiting element 34) with different elastic forces between the connecting segment 11 and the tapping segment 22. Further, with reference to FIG. 3, the distance between the connecting segment 11 and the tapping segment 22 is adjusted by rotating the fixing segment 23 to compress the limiting module 30 under different compression statuses, and this may enable the limiting module 30 to have different elastic tensions.

According to the above-mentioned structural relationship and features of the first embodiment of a force-limiting and damping device in accordance with the present invention, the limiting module 30 between the connecting segment 11 and the tapping segment 22 may provide a damping and delayed rebound effect to the reaction force, increase the contacting time of the tapping face 221 of the tapping segment 22 and the nail to prevent the nail from bending or deflecting easily, reduce noise and the loss of energy, reduce the number and time of tapping the nail, reduce the uncomfortable feel of the user and the pain of the patient, and enable the user to hold the body 10 firmly to tap. The structure of the force-limiting and damping device is simplified, and the elastic tension of the limiting module 30 can be adjusted by replacing the limiting module 30 with different elastic forces or rotating the fixing segment 23. Then, the force-limiting and damping device may provide a damping effect to a user, may provide a high stability in use, and may be easily adjusted.

In addition, when the force-limiting and damping device of the present invention is in use, at first, it can be used as a first stage of force identification by determining whether the fixing segment 23 is separated from the connecting segment 11. Whether the sleeve element 31 is in contact with the force-limiting element 34 to generate resistance is used as the force identification in a second stage. Finally, it can be rebounded immediately by judging whether the force-limiting element 34 is compressed in a third stage. The use of the force-limiting and damping device of the present invention can have a three-stage (triple) force-limiting reminding effect when in use, thereby providing a force-limiting and damping device having a reminding effect, improving feel of vibration, and adjusting force range according to the user's need.

Figure 6:
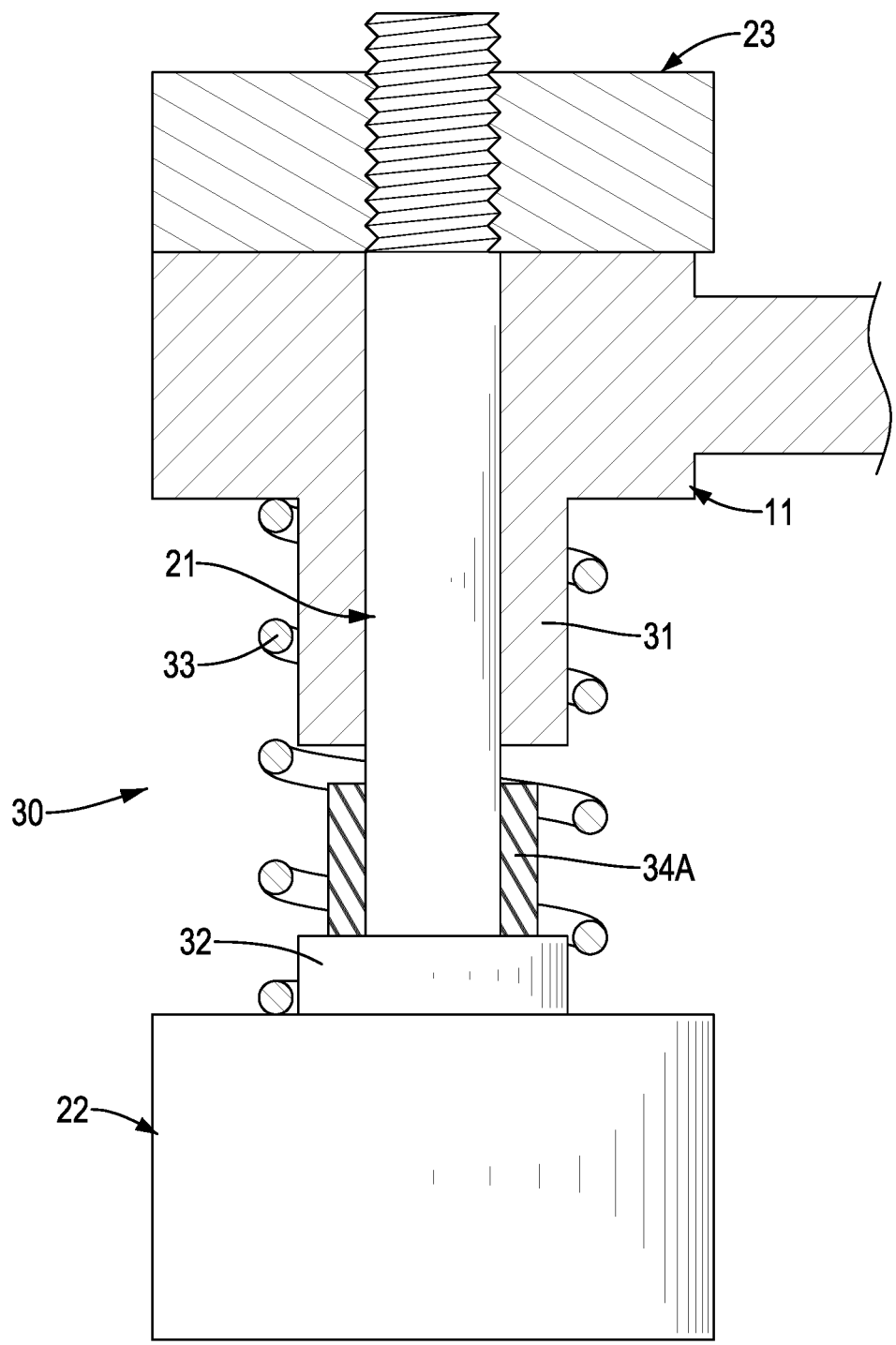
FIG. 6 is an enlarged side view in partial section of a second embodiment of a force-limiting and damping device in accordance with the present invention.

With reference to FIG. 6, a second embodiment of a force-limiting and damping device in accordance with the present invention is substantially the same as the first embodiment except for the following features. In the second embodiment of the present invention, the shock-absorbing element 33 and the force-limiting element 34 of the limiting module 30 can provide a reminding effect and improve feel of vibration without disposing the magnetic member 35 on the fixing segment 23. Furthermore, the fixing segment 23 may be connected to a component such as a washer, which is not limited herein. In addition, the force-limiting element 34A is slidably mounted on the mounting segment 21 or is securely mounted on the mounting segment 21. Further, the force-limiting element 34A is securely mounted on the positioning seat 32 and is disposed below the sleeve element 31 at a spaced interval, or is securely mounted on the sleeve element 31 and is disposed above the positioning seat 32 at a spaced interval.

Figure 7:
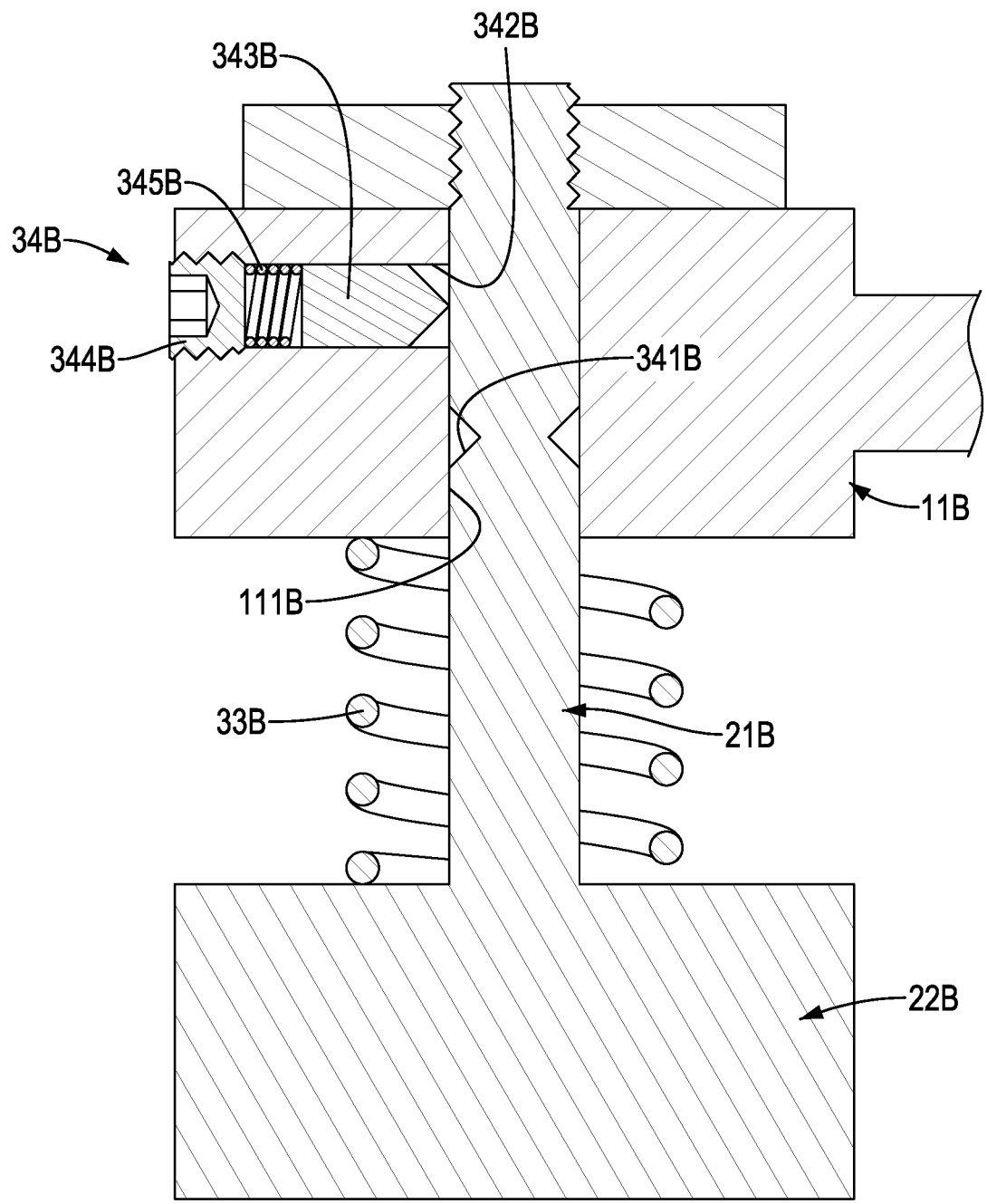
FIG. 7 is an enlarged cross sectional side view of a third embodiment of a force-limiting and damping device in accordance with the present invention.

With reference to FIG. 7, a third embodiment of a force-limiting and damping device in accordance with the present invention is substantially the same as the first embodiment except for the following features. In the third embodiment of the present invention, the force-limiting element 34B has a limiting recess 341B, a mounting recess 342B, a limiting bolt 343B, a fastener 344B, and a pushing unit 345B. The limiting recess 341B may be an annular groove, is annularly formed in the external surface of the mounting segment 21B, and has at least one inner inclined wall. The mounting recess 342B is radially formed in the connecting segment 11B, communicates with the mounting hole 111B, and has an inner thread formed in the mounting recess 342B opposite to the mounting hole 111B.

The limiting bolt 343B is movably mounted in the mounting recess 342B toward the mounting segment 21B via the mounting hole 111B, and has an inclined face selectively abutting against the at least one inner inclined wall of the limiting recess 341B. The fastener 344B is connected to the inner thread of the mounting recess 342B to prevent the limiting bolt 343B separating from the connecting segment 11B. The pushing unit 345B may be a spring, and is mounted in the mounting recess 342B between the fastener 345B and the limiting bolt 343B to push the limiting bolt 343B to abut against the external surface of the mounting segment 21B.

Figure 8:
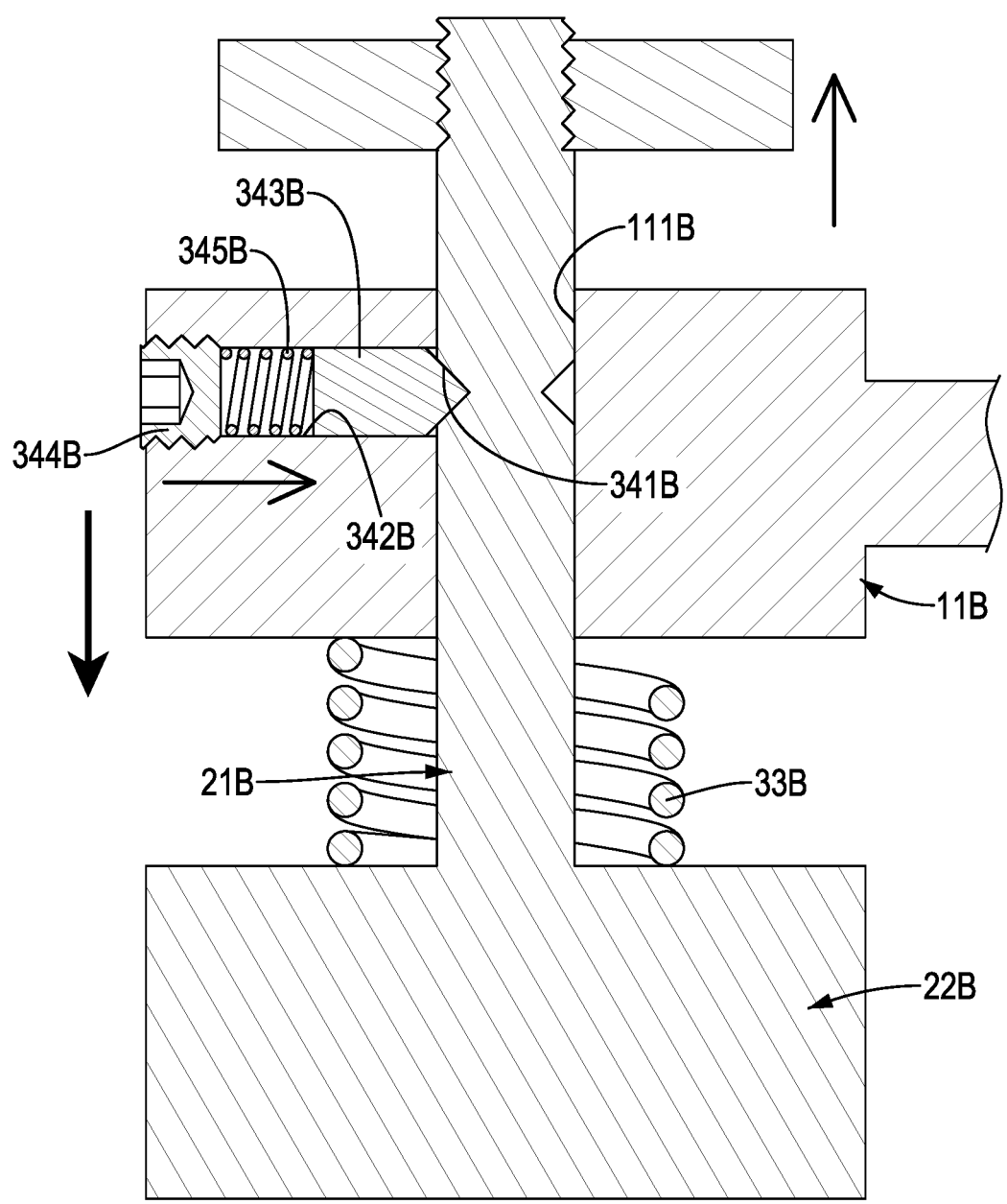
FIG. 8 is an operational cross sectional side view of the force-limiting and damping device in FIG. 7.

With reference to FIG. 8, the third embodiment of the force-limiting and damping device in accordance with the present invention is in use, when the tapping segment 22B is knocked against an object to compress the shock-absorbing element 33B, a relative movement is incurred between the connecting segment 11B and the mounting segment 21B, so the limiting recess 341B moves upwardly relative to the connecting segment 11B. When the limiting recess 341B communicates with the mounting recess 342B via the mounting hole 111B, the limiting bolt 343B engages with the limiting recess 341B by a pushing force of the pushing unit 345B to enable the inclined face of the limiting bolt 343B to abut against the inner inclined wall of the limiting recess 341B. Then a position of the tapping element 20B relative to the connecting segment 11B is limited to remind the user that the force used has exceeded the force range set by the force-limiting and damping device, and provides a reminding effect to the user.

Further, when the user's force exceeds the force range set by the force-limiting and damping device, after the limiting bolt 343B engages with the mounting segment 21B, and the user pushes the mounting segment 21B to move downwardly relative to the connecting segment 11B, the limiting bolt 343B is pushed by the mounting segment 21B and is moved toward the fastener 344B and retracted into the mounting recess 342B, so that the limiting bolt 343B is separated from the limiting recess 341B, and returned to the original position by the pushing of the shock-absorbing element 33B.

Figure 9:
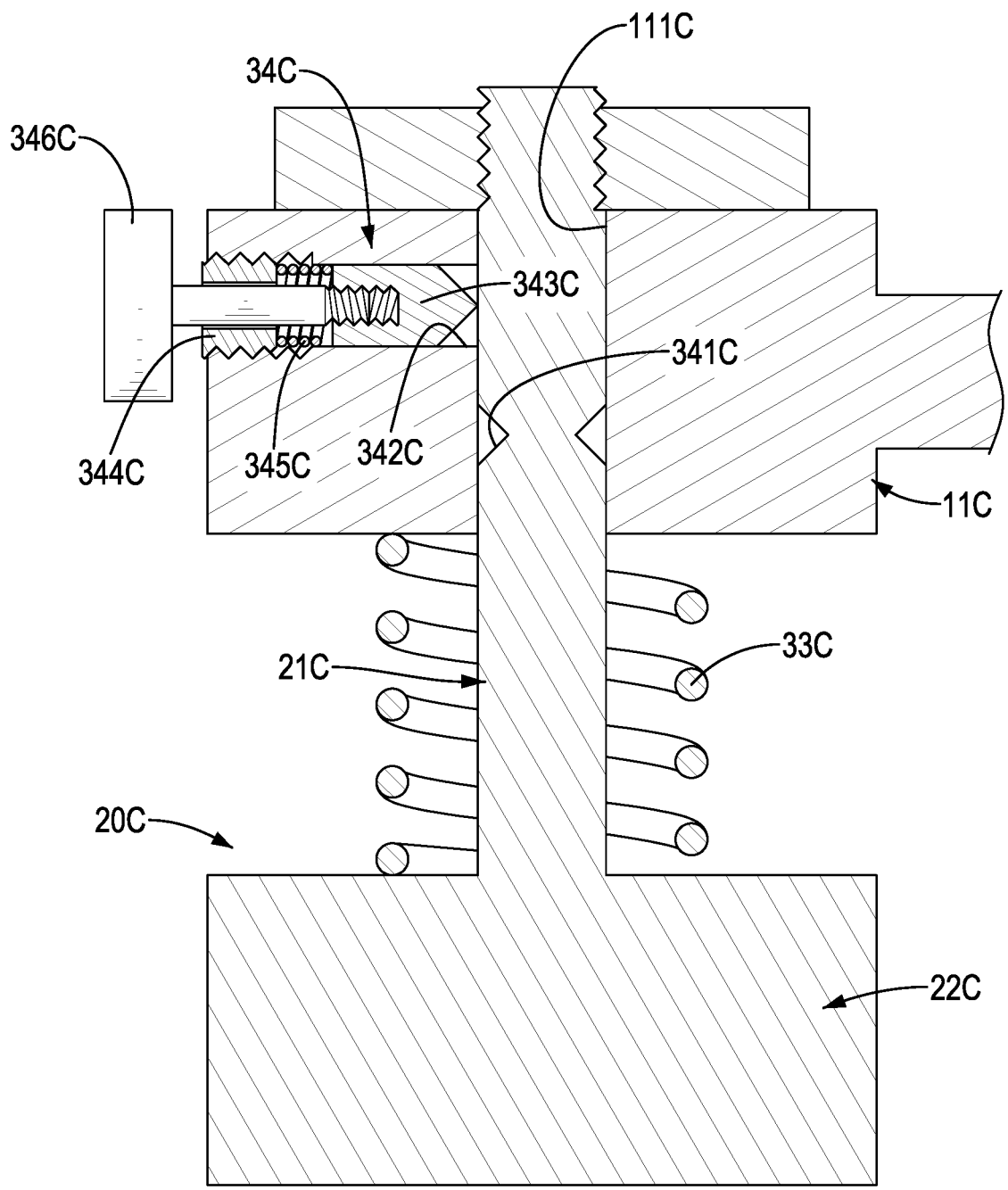
FIG. 9 is an enlarged side view in partial section of a fourth embodiment of a force-limiting and damping device in accordance with the present invention.

With reference to FIG. 9, a fourth embodiment of a force-limiting and damping device in accordance with the present invention is substantially the same as the third embodiment as shown in FIGS. 7 and 8 except for the following features. In the fourth embodiment of the present invention, the force-limiting element 34C has a pulling rod 346C. The pulling rod 346C has an inner end and an outer end. The inner end of the pulling rod 346C is securely connected to the limiting bolt 343C via the fastener 344C and the pushing unit 345C, and the outer end of the pulling rod 346C extends out of the connecting segment 11C.

Figure 10:
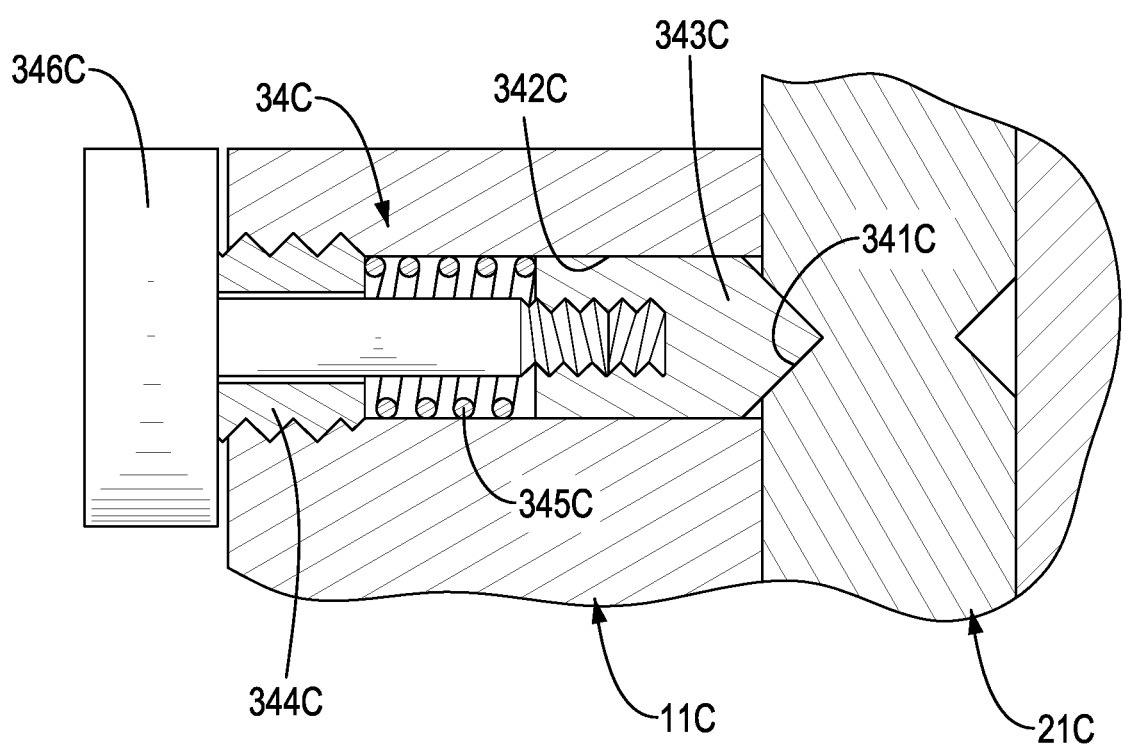
FIG. 10 is an enlarged and operational side view in partial section of the force-limiting and damping device in FIG. 9.

With reference to FIGS. 9 and 10, when the fourth embodiment of the force-limiting and damping device of the present invention is in use, when the tapping segment 22C is knocked against an object to move the mounting segment 21C relative to the connecting segment 11C, the limiting recess 341C is moved upwardly relative to the connecting segment 11C. When the limiting recess 341C communicates with the mounting recess 342C via the mounting hole 111C, the limiting bolt 343C is pushed by the pushing unit 345C to engage with the limiting recess 341C, and the inclined face of the limiting bolt 343C is abutted against the at least one inner inclined wall of the limiting recess 341C. Then a position of the tapping element 20C relative to the connecting segment 11C is limited, and the pulling rod 346C is moved toward the mounting segment 21C along with the limiting bolt 343C to remind the user that the force used has exceeded the force range set by the force-limiting and damping device, and provides a reminding effect to the user.

Furthermore, when the user's force exceeds the force range set by the force-limiting and damping device, after the limiting bolt 343C engages with the mounting segment 21C, the user can pull the pushing rod 346C to pull the limiting bolt 343C toward the fastener 344C, retract into the mounting recess 342C, and separate from the limiting recess 341C. Then the mounting segment 21C can be moved downwardly relative to the connecting segment 11C back to the original position by the pushing force of the shock-absorbing element 33C.

Figure 11:
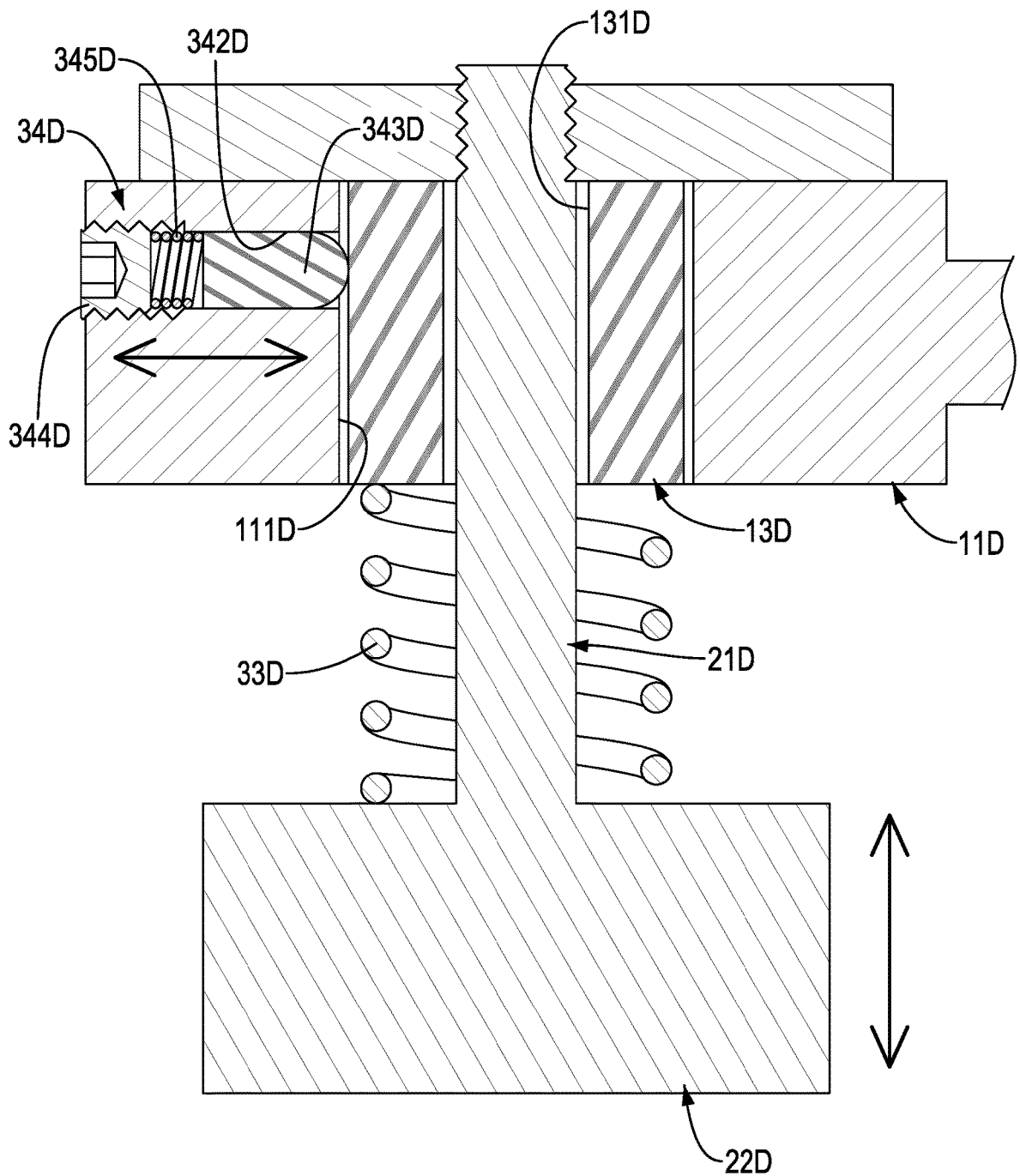
FIG. 11 is an enlarged cross sectional side view of a fifth embodiment of a force-limiting and damping device in accordance with the present invention.

With reference to FIG. 11, a fifth embodiment of a force-limiting and damping device in accordance with the present invention is substantially the same as the third embodiment as shown in FIGS. 7 and 8 except for the following features. In the fourth embodiment of the present invention, the connecting segment 11D has a limiting block 13D disposed between the mounting hole 111D and the mounting segment 21D. Preferably, the limiting block 13D may be a bushing. Further, the limiting block 13D is mounted in the mounting hole 111D of the connecting segment 11D and has a communicating hole 131D formed through the limiting block 13D and mounted around the mounting segment 21D. A gap is formed between the communicating hole 131D and the mounting segment 21D, and the shock-absorbing element 33D abuts against the limiting block 13D.

Additionally, the limiting block 34D in the fifth embodiment of the present invention does not have a limiting recess, and the limiting bolt 343D abuts against an external surface of the limiting block 13D. When the tapping segment 22D is knocked against an object to compress the shock-absorbing element 33D, since the limiting block 13D abuts against the limiting bolt 343D and has frictional force, the frictional force between the limiting block 13D and the limiting bolt 343D can provide a force limiting effect to the shock-absorbing element 33D when the tapping segment 22D moves relative to the connecting segment 11D.

Figure 12:
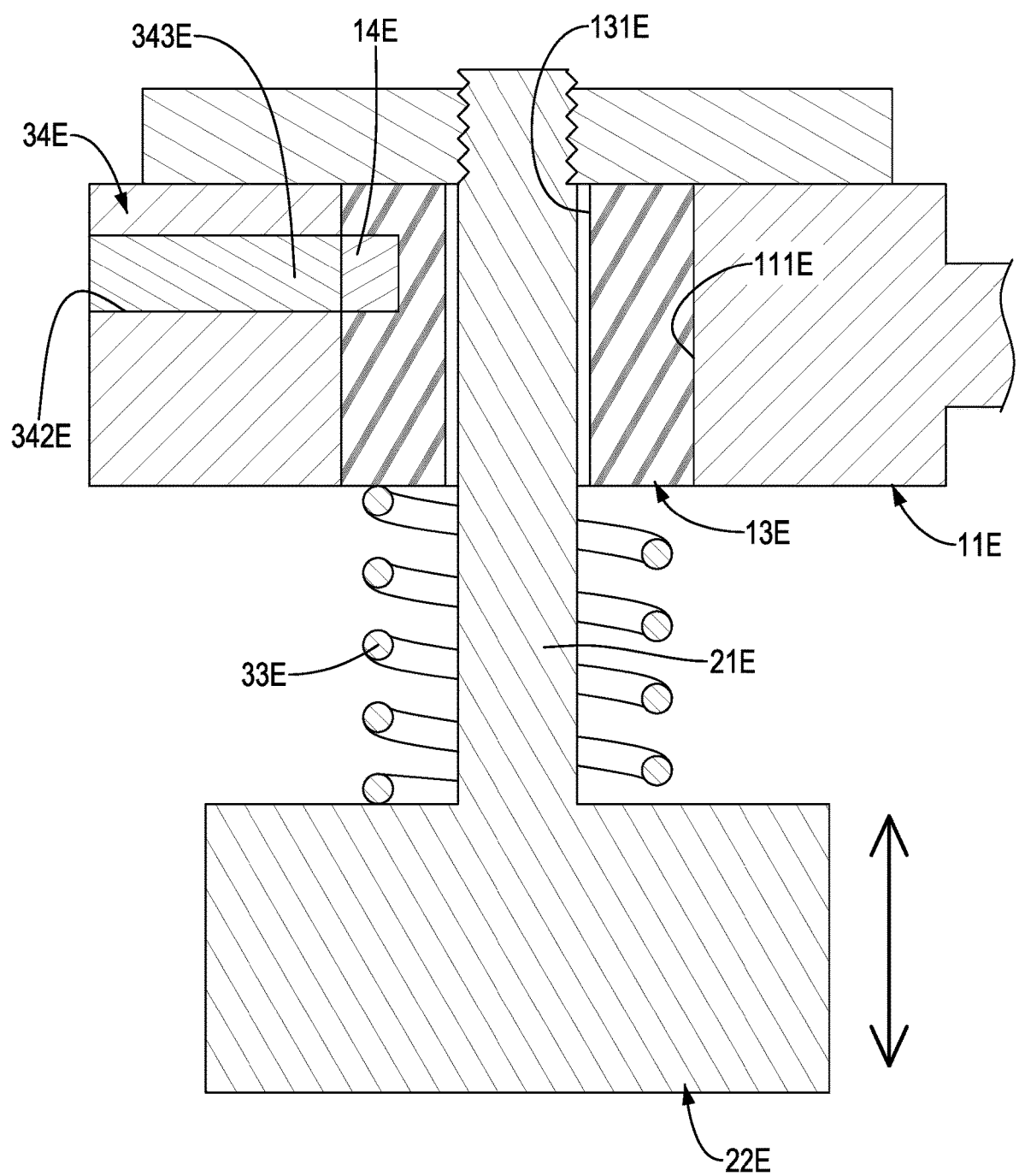
FIG. 12 is an enlarged cross sectional side view of a sixth embodiment of a force-limiting and damping device in accordance with the present invention.

With reference to FIG. 12, a sixth embodiment of a force-limiting and damping device in accordance with the present invention is substantially the same as the fifth embodiment as shown in FIG. 11 except for the following features. In the sixth embodiment of the present invention, the force-limiting element 34E does not have a fastener and a pushing unit, the limiting bolt 343E is mounted in the mounting recess 342E, the limiting block 13E has a magnetic element 14E disposed in an external surface of the limiting block 13E, faced to and magnetically attracted to the limiting bolt 343E. When the tapping segment 22E is knocked against an object to compress the shock-absorbing element 33E, due to the magnetic attraction caused by the magnetic element 14E and the limiting bolt 343E attracting each other, the magnetic force between the limiting block 13E and the limiting bolt 343E can provide a force limiting effect to the shock-absorbing element 33E when the tapping segment 22E moves relative to the connecting segment 11E.

Figure 13:
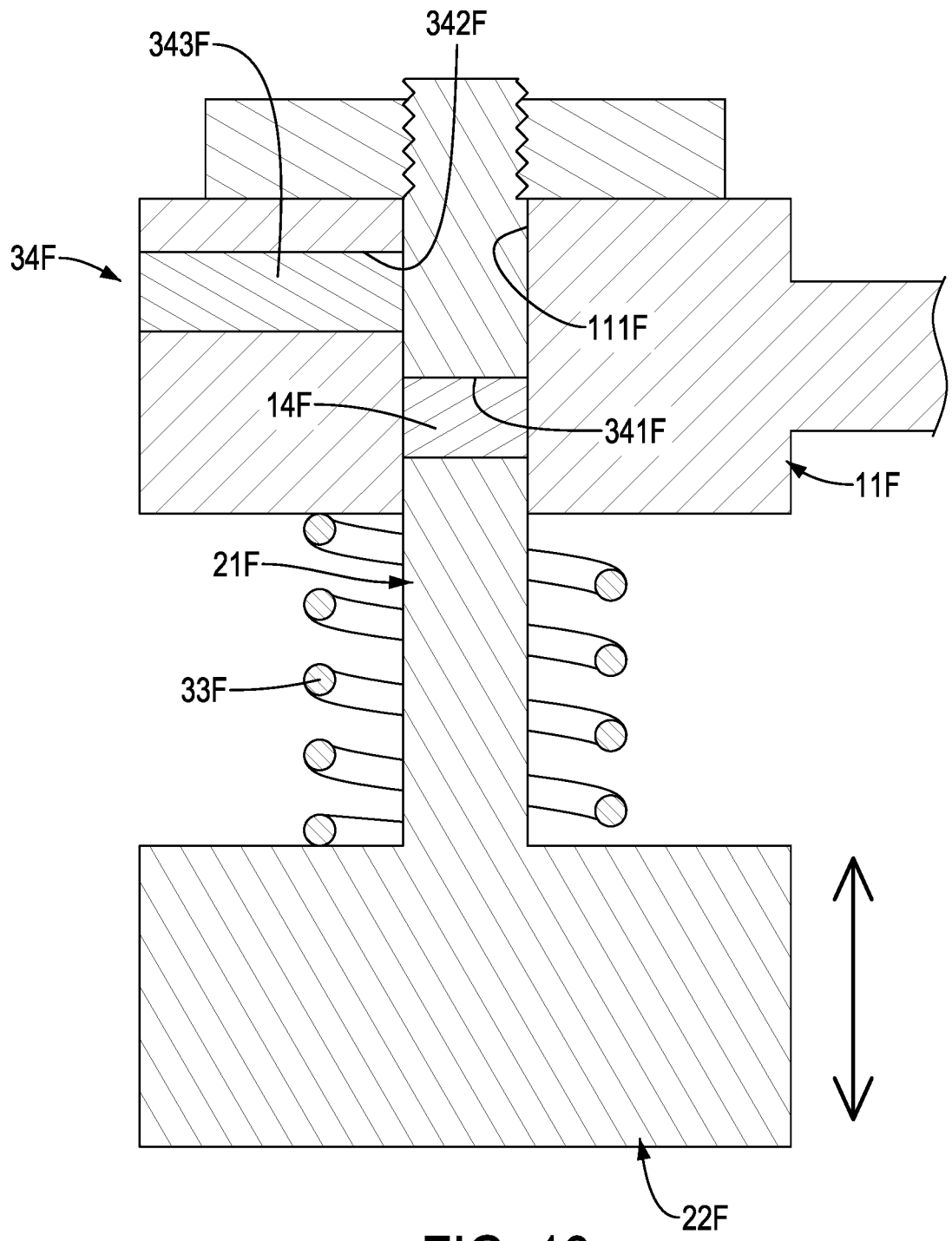
FIG. 13 is an enlarged cross sectional side view of a seventh embodiment of a force-limiting and damping device in accordance with the present invention.

With reference to FIG. 13, a seventh embodiment of a force-limiting and damping device in accordance with the present invention is substantially the same as the sixth embodiment as shown in FIG. 12 except for the following features. In the seventh embodiment of the present invention, the connecting segment 11F does not have a limiting block, the limiting recess 341F of the force-limiting element 34F is radially formed through the mounting segment 21F, the magnetic element 14F is mounted in the limiting recess 341F, and the limiting bolt 343F is mounted in the mounting recess 342F.

When the mounting segment 21F is moved relative to the connecting segment 11F, the magnetic element 14F is moved with the mounting segment 21F to align with the limiting bolt 343F, and the limiting bolt 343F is a magnetic block. When the tapping segment 22F is knocked against an object to compress the shock-absorbing element 33F, due to the magnetic attraction caused by the magnetic element 14F and the limiting bolt 343F attracting each other when the magnetic element 14F is moved with the mounting segment 21F to align with the limiting bolt 343F, the magnetic force between the limiting block 13F and the limiting bolt 343F can provide a force limiting effect to the shock-absorbing element 33F.

Figure 14:
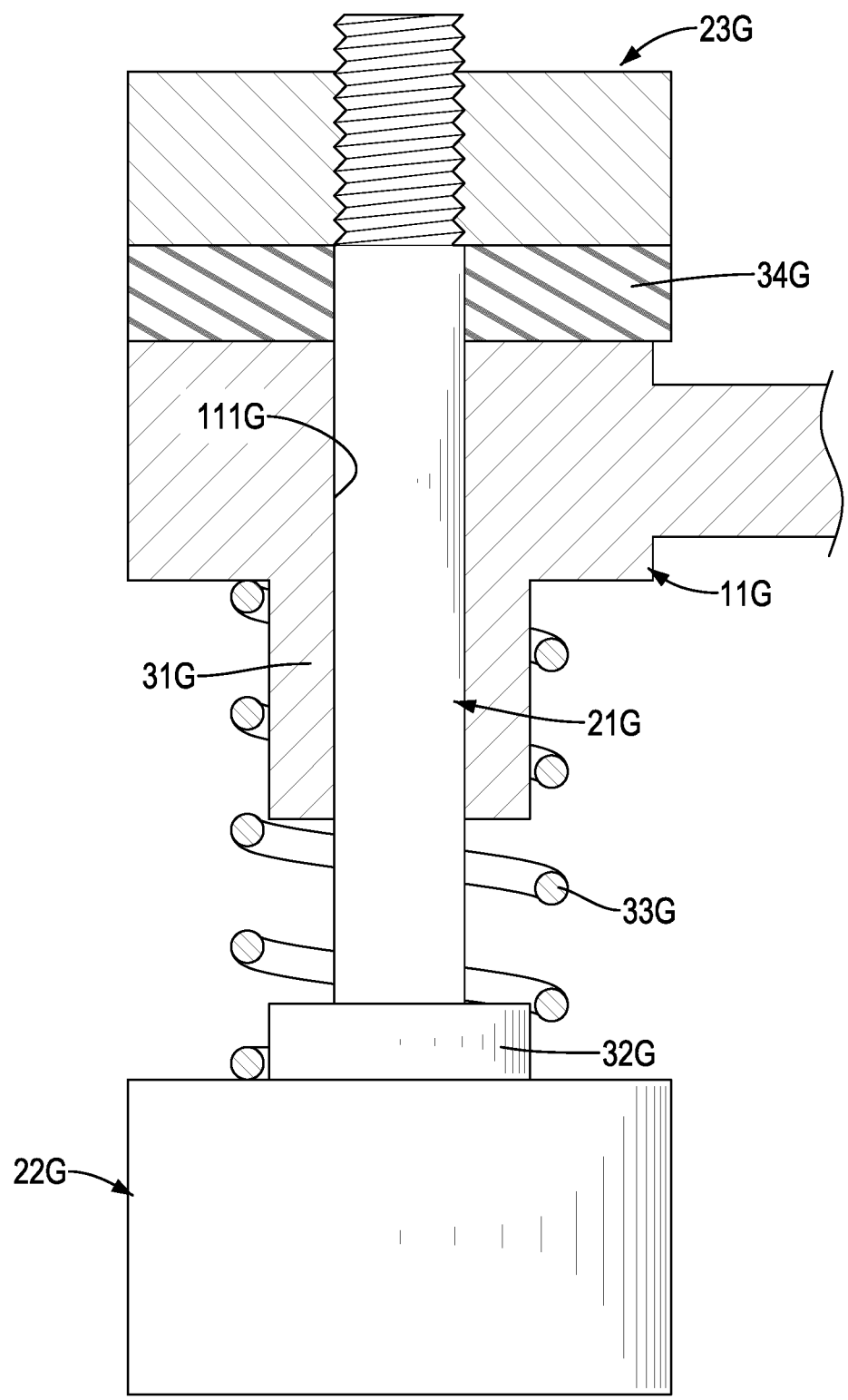
FIG. 14 is an enlarged side view in partial section of an eighth embodiment of a force-limiting and damping device in accordance with the present invention.

With reference to FIG. 14, an eighth embodiment of a force-limiting and damping device in accordance with the present invention is substantially the same as the second embodiment as shown in FIG. 6 except for the following features. In the eighth embodiment of the present invention, the force-limiting element 34G may be made of flexible material in a fixed shape such as a spring, rubber, silicone, a metal washer, a flexible metal block or a flexible block. Furthermore, the spring may be mounted in the rubber or the silicone to form the force-limiting element 34G and is mounted on the mounting segment 21G between the fixing segment 23G and the connecting segment 11G rather than the sleeve element 31G and the positioning seat 32G When the tapping segment 22G is knocked against an object to compress the shock-absorbing element 33G, the fixing segment 23G is separated from the force-limiting element 34G along with the mounting segment 21G and the compressed shock-absorbing element 33G can provide a restoring force to the tapping segment 22G, thereby driving the fixing segment 23G disposed on the mounting segment 21G to move toward the connecting segment 11G. The force-limiting element 34G disposed between the fixing segment 23G and the connecting segment 11G can prevent the fixing segment 23G from knocking against the connecting segment 11G during the tapping process to reduce the damage caused by the collision. In addition, the force-limiting element 34G may provide a space for the tapping segment 20 to extend outward, thereby prolonging the contacting time between the tapping segment 22G and a nail, so that the elastic potential energy stored by the shock-absorbing element 33G can be effectively transformed into the kinetic energy of the nail.

Further, when the sleeve element 31G is knocked against the positioning seat 32G during the tapping process, the user will feel the reaction force of instant rebound, and this can provide a reminder effect of the limitation of knocking force to the user. When the user wants to knock the object with great force, the collision between the sleeve element 31G and the positioning seat 32G can convey an impact effect of unlimited force. Moreover, before the sleeve element 31G is knocked against the positioning seat 32G, the shock-absorbing element 33G disposed between the tapping segment 22G and the connecting segment 11G can avoid the reaction force that instantly rebounds at the beginning of the tapping process to reduce the occurrence of bouncing of nails. Different force limiting effects of the force-limiting and damping device of the present invention can be provided by adjusting the distance between the sleeve element 31G and the positioning seat 32 and the elastic strength of the shock-absorbing element 33G, and the force-limiting and damping device can also be used without using the force-limiting element 34G.

Figure 15:
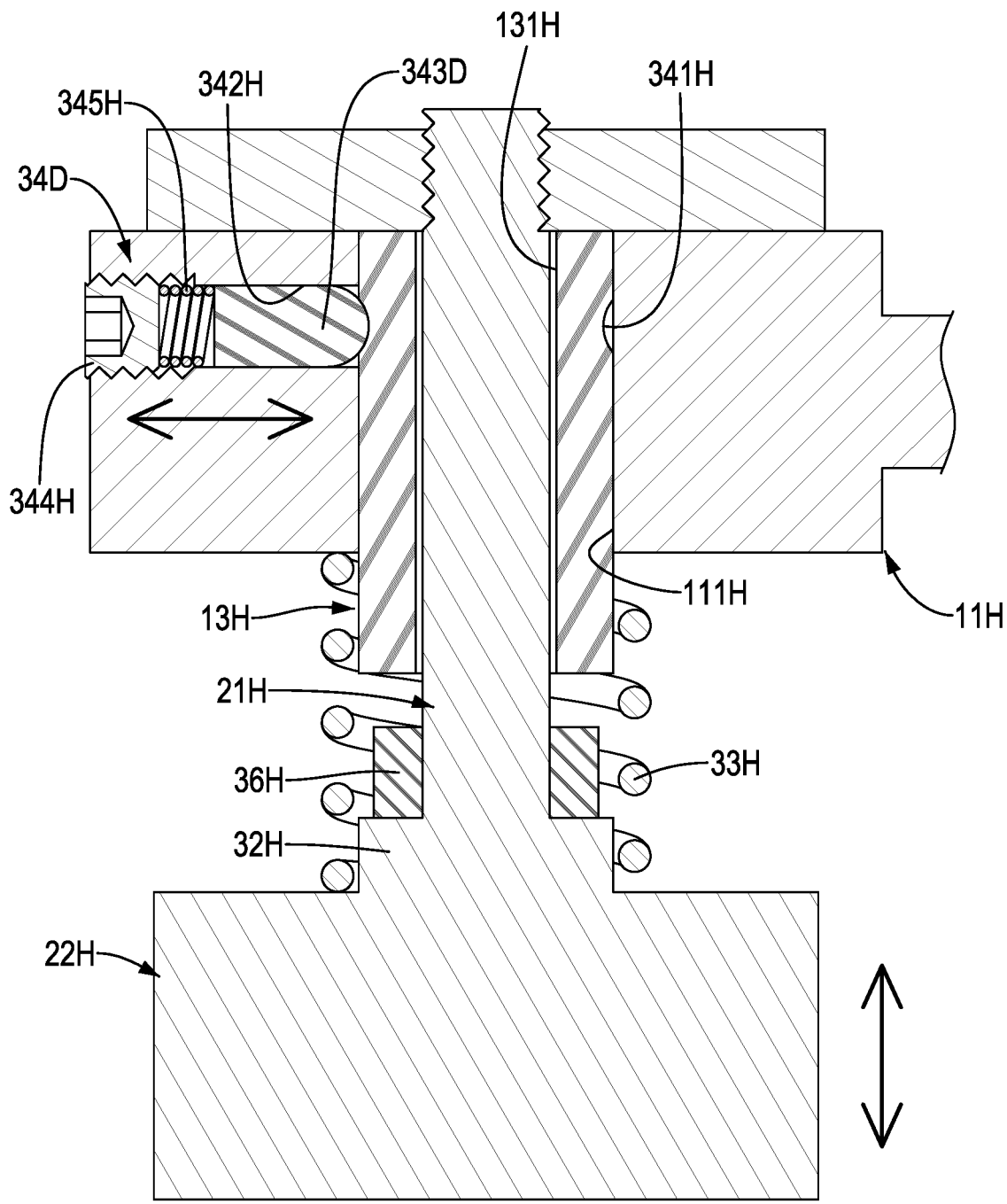
FIG. 15 is an enlarged cross sectional side view of a ninth embodiment of a force-limiting and damping device in accordance with the present invention.

With reference to FIG. 15, a ninth embodiment of a force-limiting and damping device in accordance with the present invention is substantially the same as the fifth embodiment as shown in FIG. 11 except for the following features. In the ninth embodiment of the present invention, a bottom of the limiting block 13H extends out of the bottom side of the connecting segment 11H via the mounting hole 111H, the shock-absorbing element 33H is mounted around the limiting block 13H, and the limiting recess 341H of the force-limiting element 34H is annularly formed on the external surface of the limiting block 13H. Then the limiting blot 343H abuts against the limiting block 13H at the limiting recess 341H. Furthermore, the force-limiting and damping device has an auxiliary element 36H mounted on the mounting segment 21H between the shock-absorbing element 33H and the positioning seat 32H to provide an auxiliary damping effect to the force-limiting and damping device.

Figure 16:
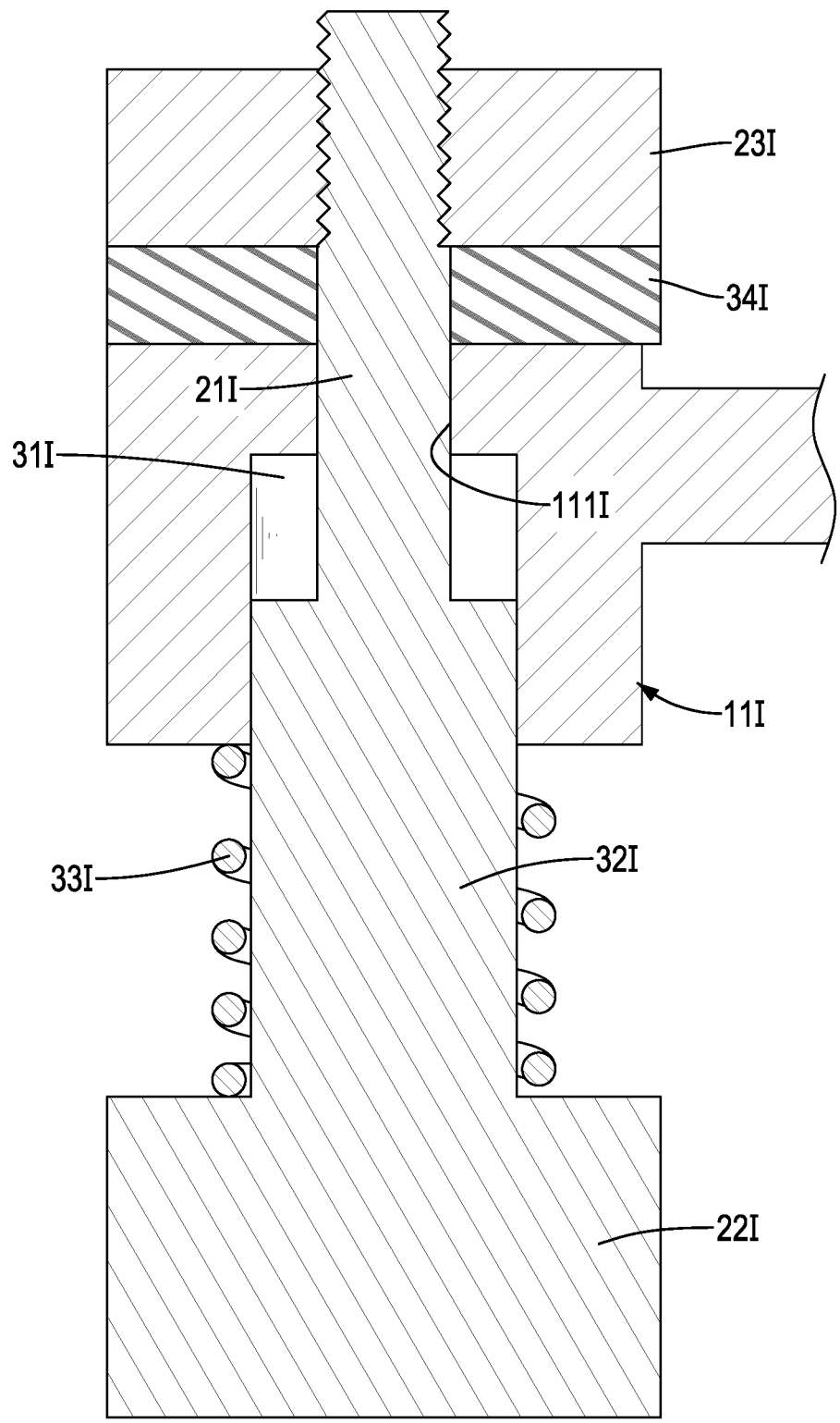
FIG. 16 is an enlarged cross sectional side view of a tenth embodiment of a force-limiting and damping device in accordance with the present invention.

With reference to FIG. 16, a tenth embodiment of a force-limiting and damping device in accordance with the present invention is substantially the same as the eighth embodiment as shown in FIG. 14 except for the following features. In the tenth embodiment of the present invention, the sleeve element 31I is a recessed structure and is formed in the connecting segment 11I via the bottom side of the connecting segment 11I, the positioning seat 32I extends into the sleeve element 31I via the bottom side of the connecting segment 11I, and a distance is formed between the sleeve element 31I and the positioning seat 32I.

When the tapping segment 22I is knocked against an object to compress the shock-absorbing element 33I, the shock-absorbing element 33I can provide a restoring force to the tapping segment 22I, thereby driving the fixing segment 23I disposed on the mounting segment 21I to move toward the connecting segment 11I. The force-limiting element 34I disposed between the fixing segment 23I and the connecting segment 11I can prevent the fixing segment 23I from knocking against the connecting segment 11I during the tapping process to reduce the damage caused by the collision.

Further, when the sleeve element 31GI is knocked against the positioning seat 32I during the tapping process, the user will feel the reaction force of instant rebound, and this can provide a reminder effect of the limitation of knocking force to the user. When the user wants to knock the object with great force, the collision between the sleeve element 31I and the positioning seat 32I can convey an impact effect of unlimited force. Moreover, before the sleeve element 31I is knocked against the positioning seat 32I, the shock-absorbing element 33I disposed between the tapping segment 22I and the connecting segment 11I can avoid the reaction force that instantly rebounds at the beginning of the tapping process to reduce the occurrence of bouncing of nails. Different force limiting effects of the force-limiting and damping device of the present invention can be provided by adjusting the distance between the sleeve element 31I and the positioning seat 32I and the elastic strength of the shock-absorbing element 33I, and the force-limiting and damping device can also be used without using the force-limiting element 34I.

Figure 17:
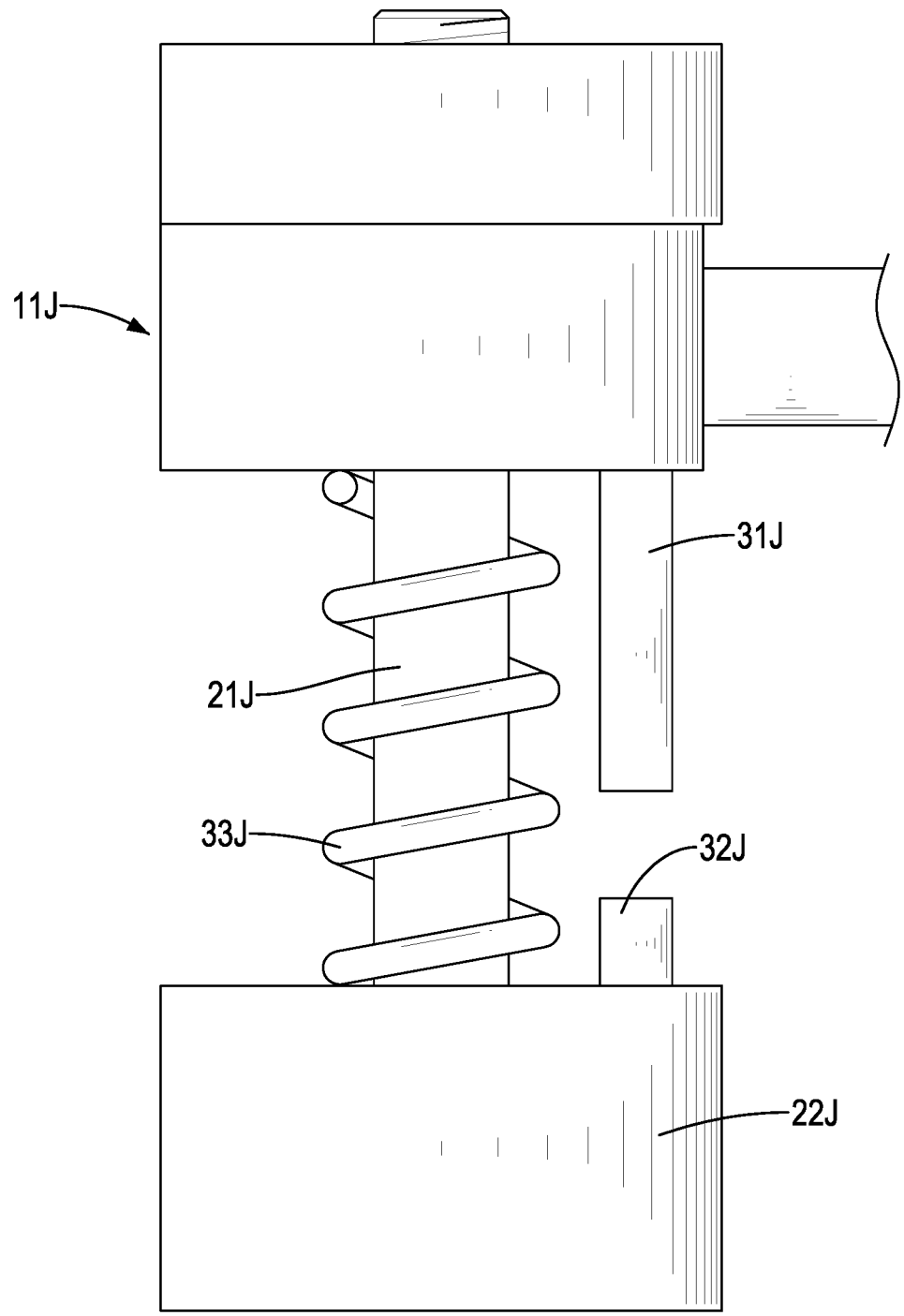
FIG. 17 is an enlarged side view of an eleventh embodiment of a force-limiting and damping device in accordance with the present invention.

With reference to FIG. 17, an eleventh embodiment of a force-limiting and damping device in accordance with the present invention is substantially the same as the first embodiment as shown in FIG. 3 except for the following features. In the eleventh embodiment of the present invention, the sleeve element 31J is integrally or separately disposed at the bottom side of the connecting segment 11J, and is located at one side of the mounting segment 21J or is annularly arranged around the external surface of the mounting segment 21J. The positioning seat 32J is integrated or separately disposed on the tapping segment 22J, and is located at one side of the mounting segment 21J or is annularly arranged around the external surface of the mounting segment 21J and is disposed below the sleeve element 31J at a spaced interval.

Figure 18:
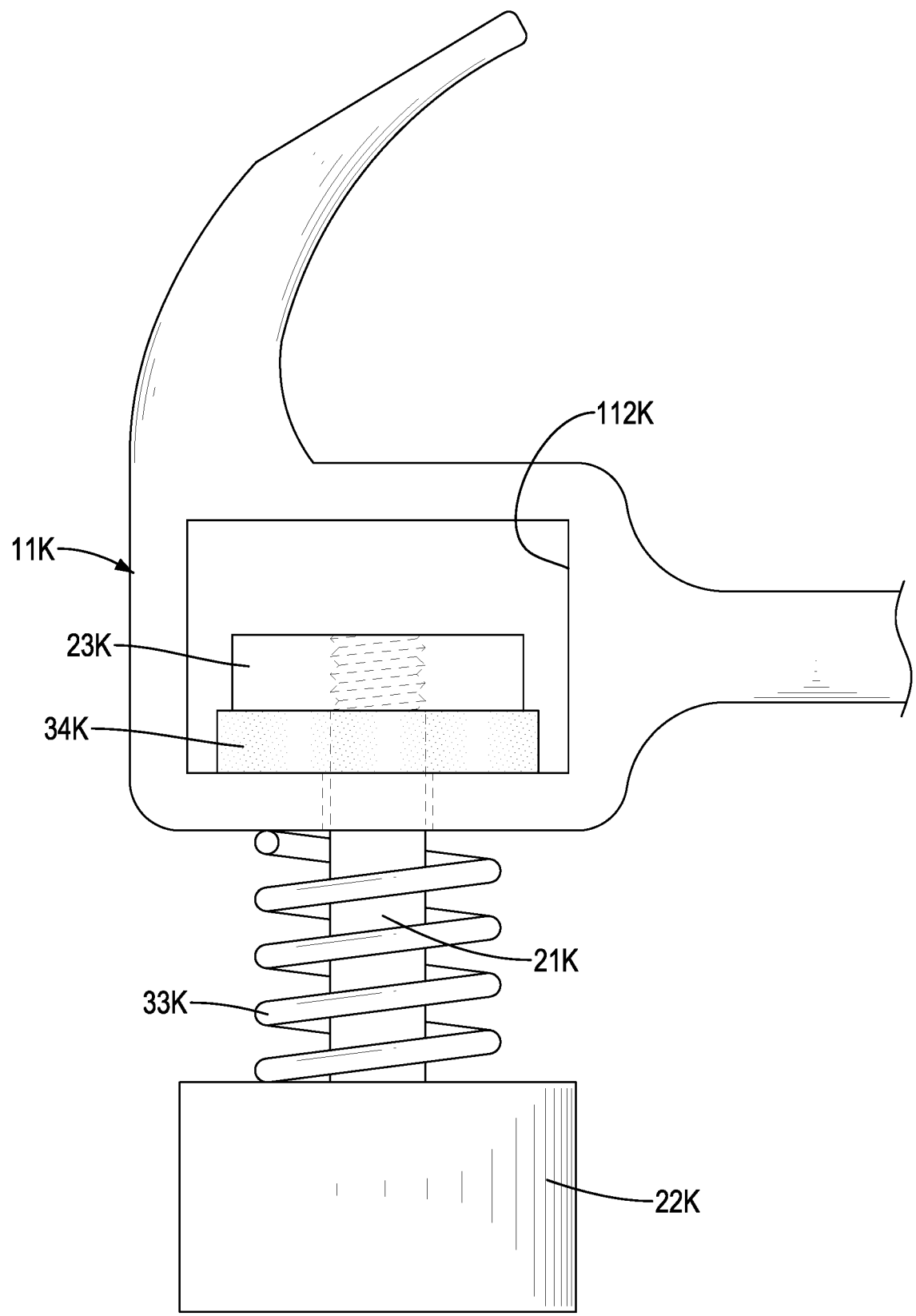
FIG. 18 is an enlarged side view of a twelfth embodiment of a force-limiting and damping device in accordance with the present invention.

With reference to FIG. 18, a twelfth embodiment of a force-limiting and damping device in accordance with the present invention is substantially the same as the first embodiment as shown in FIG. 3 except for the following features. In the twelfth embodiment of the present invention, the connecting segment 11K has a through slot 112K transversally formed through a sidewall of the connecting segment 11K, the mounting segment 21K extends into the through slot 112K via the bottom side of the connecting segment 11K, the fixing segment 23K is connected to the mounting segment 21K in the through slot 112K, and the force-limiting element 34K is mounted around the mounting segment 21K between the fixing segment 23K and the connecting segment 11K at the through slot 112K. The fixing segment 23K will knock against a top of the through slot 112K when the knocking force is too large, and this may provide a reminder effect of the limitation of knocking force to the user, and can provide an unlimited force. In addition, the force-limiting element 34K between the connecting segment 11K and the fixing segment 23K also can absorb the vibration during the tapping process to avoid damage to the fixing segment 23K. Additionally, in the above-mentioned embodiments of the present invention, the shock-absorbing element 33, 33B, 33C, 33D, 33E, 33F, 33G 33H, 33I, 33J, 33K and the force-limiting element 34, 34A, 34B, 34C, 34D, 34E, 34F, 34G, 34H, 34I, 34K may be made of flexible material in a fixed shape such as a spring, rubber, silicone, a metal washer, a flexible metal block or a flexible block. Furthermore, the spring may be mounted in the rubber or the silicone to form the shock-absorbing element 33, 33B, 33C, 33D, 33E, 33F, 33G, 33H, 33I, 33J, 33K and the force-limiting element 34, 34A, 34B, 34C, 34D, 34E, 34F, 34G, 34H, 34I, 34K. Further, each one of the shock-absorbing element 33, 33B, 33C, 33D, 33E, 33F, 33G, 33H, 33I, 33J, 33K and the force-limiting element 34, 34A, 34B, 34C, 34D, 34E, 34F, 34G 34H, 34I, 34K can be selected from one of the aforementioned flexible materials, and the present invention does not limit the arrangement.

Additionally, when the shock-absorbing element 33, 33B, 33C, 33D, 33E, 33F, 33G, 33H, 33I, 33J, 33K and the force-limiting element 34, 34A, 34B, 34C, 34D, 34E, 34F, 34G, 34H, 34I of the above-mentioned embodiments of the present invention are compressed to maximum limits during a tapping process, an unlimited tapping effect can be provided.

According to the above-mentioned structural relationships and the features, the structure of the force-limiting and damping device is simplified, and this is convenient in manufacture, maintenance and replacement. Furthermore, the limiting module 30 is mounted between the connecting segment 11, 11B, 11C, 11D, 11E, 11F, 11G 11H, 11I, 11K of the body 10 and the tapping segment 22, 22B, 22C, 22D, 22E, 22F, 22G, 22H, 22I, 22J, 22K of the tapping element 20, 20C. Then, the user's may be reminded of the tapping force by observing the compression extent of the limiting module 30, and this may provide a force-limiting effect to the user. In addition, the force-limiting and damping device may provide a delayed rebound and damping effect to the reaction force that is generated when the tapping segment 22, 22B, 22C, 22D, 22E, 20E', 22F, 22G, 22J, 22K, 22M is tapped on an object, and this may increase the contacting time between the tapping segment 22, 22B, 22C, 22D, 22E, 22F, 22G, 22H, 22I, 22J, 22K and the object to prevent the object from bending or deflecting, and reduce noise and the loss of energy. Furthermore, the number and time of tapping the object can be reduced relatively.

Additionally, the force-limiting and damping device may reduce the uncomfortable feel of the user and the pain of the patient, and the user may hold the body 10 securely to tap. Further, the force-limiting and damping device is simplified and may provide different elastic tensions of the limiting module 30 by replacing the elastic element 30 with different elastic forces or by rotating the fixing segment 23, 23G, 23I, 23K easily. Therefore, the force-limiting and damping device of the present invention may provide a reminder effect to a user, may improve feel of vibration, and may adjust the force range according to the user's need.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A force-limiting and damping device comprising:
   a body, being an elongated shaft and having
      a front end;
      a rear end;
      a connecting segment formed on and protruding from the front end of the body and having
         a top side;
         a bottom side;
         an external surface; and
         a mounting hole formed through the top side and the bottom side of the connecting segment; and
      a holding segment formed on the rear end of the body and being opposite the connecting segment;
   a tapping element connected to the body to move relative to the connecting segment and having
      a mounting segment movably connected to the mounting hole of the connecting segment;
      a tapping segment disposed on an end of the mounting segment below the connecting segment; and
      a fixing segment connected to the mounting segment and abutting the connecting segment;
   a shock-absorbing element mounted on the mounting segment, abutting the connecting segment of the body and the tapping segment of the tapping element, and having a preset compression force; and
   wherein when a tapping force is smaller than the preset compression force of the shock-absorbing element, the tapping segment generates an instant rebound, and when the tapping force is larger than the preset compression force of the shock-absorbing element, the tapping segment generates a delayed rebound;
   a limiting module mounted between the body and the tapping element and having
      a sleeve element formed on and protruding from the bottom side of the connecting segment and having a through hole formed through the sleeve element and communicating with the mounting hole of the connecting segment;
      a positioning seat formed on a connecting position between the mounting segment and the tapping segment, and disposed below the sleeve element at a spaced interval; and
      a force-limiting element non-contacted with the shock-absorbing element;
   wherein the force-limiting element is mounted on the mounting segment between the sleeve element and the positioning seat;
   wherein the force-limiting and damping device has at least two-stage force-limiting reminding effect when in use, a first stage of force identification is determined by whether the shock-absorbing element is compressed between the connecting segment and the tapping segment, and a second stage of force identification is determined by whether the force-limiting element is compressed between the connecting segment and the tapping segment.

2. The force-limiting and damping device as claimed in claim 1, wherein the limiting module has at least one magnetic member, and the at least one magnetic member is disposed on the fixing segment to attract the connecting segment by a magnetic attracting force between the at least one magnetic member and the connecting segment to provide a force-limiting reminder effect.

3. The force-limiting and damping device as claimed in claim 2, wherein the force-limiting element is a spring, an annular rubber block, a silicone block, a flexible metal block, a flexible block or a bushing.

4. The force-limiting and damping device as claimed in claim 3, wherein the force-limiting element is slidably mounted on the mounting segment.

5. The force-limiting and damping device as claimed in claim 4, wherein the force-limiting element is securely mounted on the positioning seat and is disposed below the sleeve element at a spaced interval.

6. The force-limiting and damping device as claimed in claim 4, wherein the force-limiting element is securely mounted on the sleeve element and is disposed above the positioning seat at a spaced interval.

7. The force-limiting and damping device as claimed in claim 3, wherein the force-limiting element is securely mounted on the mounting segment.

8. The force-limiting and damping device as claimed in claim 2, wherein the force-limiting element is slidably mounted on the mounting segment.

9. The force-limiting and damping device as claimed in claim 8, wherein the force-limiting element is securely mounted on the positioning seat and is disposed below the sleeve element at a spaced interval.

10. The force-limiting and damping device as claimed in claim 8, wherein the force-limiting element is securely mounted on the sleeve element and is disposed above the positioning seat at a spaced interval.

11. The force-limiting and damping device as claimed in claim 2, wherein the force-limiting element is securely mounted on the mounting segment.

12. The force-limiting and damping device as claimed in claim 1, wherein the force-limiting element is a spring, an annular rubber block, a silicone block, a flexible metal block, a flexible block or a bushing.

13. The force-limiting and damping device as claimed in claim 12, wherein the force-limiting element is slidably mounted on the mounting segment.

14. The force-limiting and damping device as claimed in claim 13, wherein the force-limiting element is securely mounted on the positioning seat and is disposed below the sleeve element at a spaced interval.

15. The force-limiting and damping device as claimed in claim 13, wherein the force-limiting element is securely mounted on the sleeve element and is disposed above the positioning seat at a spaced interval.

16. The force-limiting and damping device as claimed in claim 12, wherein the force-limiting element is securely mounted on the mounting segment.

17. The force-limiting and damping device as claimed in claim 1, wherein the force-limiting element is slidably mounted on the mounting segment.

18. The force-limiting and damping device as claimed in claim 1, wherein the force-limiting element is securely mounted on the positioning seat and is disposed below the sleeve element at a spaced interval.

19. The force-limiting and damping device as claimed in claim 1, wherein the force-limiting element is securely mounted on the sleeve element and is disposed above the positioning seat at a spaced interval.

20. The force-limiting and damping device as claimed in claim 1, wherein the force-limiting element is securely mounted on the mounting segment.

21. The force-limiting and damping device as claimed in claim 1, wherein the force-limiting element has
   a limiting recess annularly formed in an external surface of the mounting segment and having at least one inner inclined wall;
   a mounting recess radially formed in the connecting segment;
   a limiting bolt movably mounted in the mounting recess toward the mounting segment via the mounting hole and having an inclined face selectively abutting against the at least one inner inclined wall of the limiting recess;
   a fastener mounted in the mounting recess opposite to the limiting bolt; and
   a pushing unit mounted in the mounting recess between the fastener and the limiting bolt to push the limiting bolt to abut against the external surface of the mounting segment via the mounting hole.

22. The force-limiting and damping device as claimed in claim 1, wherein the force-limiting element has
   a limiting recess annularly formed in an external surface of the mounting segment and having at least one inner inclined wall;
   a mounting recess radially formed in the connecting segment;
   a limiting bolt movably mounted in the mounting recess toward the mounting segment via the mounting hole and having an inclined face selectively abutting against the at least one inner inclined wall of the limiting recess;
   a fastener mounted in the mounting recess opposite to the limiting bolt;
   a pushing unit mounted in the mounting recess between the fastener and the limiting bolt to push the limiting bolt to abut against the external surface of the mounting segment via the mounting hole; and
   a pulling rod having an inner end securely connected to the limiting bolt via the fastener and the pushing unit and an outer end extending out of the connecting segment.

23. The force-limiting and damping device as claimed in claim 1, wherein
   the connecting segment has a limiting block disposed between the mounting hole and the mounting segment, and the limiting block is mounted in the mounting hole of the connecting segment and has a communicating hole formed through the limiting block and located around the mounting segment; and
   the force-limiting element has
      a mounting recess radially formed in the connecting segment and communicating with the mounting hole;
      a limiting bolt movably mounted in the mounting recess and abutting against an external surface of the limiting block;
      a fastener mounted in the mounting recess opposite to the limiting bolt; and
      a pushing unit mounted in the mounting recess between the fastener and the limiting bolt to push the limiting bolt to abut against the external surface of the limiting block via the mounting hole.

24. The force-limiting and damping device as claimed in claim 23, wherein the limiting block has a magnetic element disposed in the external surface of the limiting block, the magnetic element faced to and magnetically attracted to the limiting bolt.

25. The force-limiting and damping device as claimed in claim 23, wherein
   the limiting block has a bottom extending out of the bottom side of the connecting segment via the mounting hole;
   the shock-absorbing element is mounted around the limiting block;
   the force-limiting element has a limiting recess annularly formed on the external surface of the limiting block; and
   the limiting bolt abuts against the limiting block at the limiting recess.

26. The force-limiting and damping device as claimed in claim 25, wherein
   the limiting module has a positioning seat formed on a connecting position between the mounting segment and the tapping segment; and
   the force-limiting and damping device has an auxiliary element mounted on the mounting segment between the shock-absorbing element and the positioning seat.

27. The force-limiting and damping device as claimed in claim 1, wherein
   the force-limiting element has
      a limiting recess radially formed through the mounting segment;
      a mounting recess radially formed in the connecting segment; and
      a limiting bolt being magnetic and mounted in the mounting recess; and
   the mounting segment has a magnetic element mounted in the limiting recess and aligning with the limiting bolt when the mounting segment is moved relative to the connecting segment.

28. The force-limiting and damping device as claimed in claim 1, wherein the force-limiting element is mounted on the mounting segment between the fixing segment and the connecting segment.

29. The force-limiting and damping device as claimed in claim 28, wherein
   the limiting module has
      a sleeve element being a recessed structure and formed in the connecting segment via the bottom side of the connecting segment; and
      a positioning seat formed on a connecting position between the mounting segment and the tapping segment, and extending into the sleeve element via the bottom side of the connecting segment;
   a distance is formed between the sleeve element and the positioning seat; and
   the shock-absorbing element is mounted around the positioning seat and abuts the connecting segment and the tapping segment.

30. The force-limiting and damping device as claimed in claim 1, wherein the tapping segment of the tapping element is a spheroid or is flat, axe-like, curved or tapered.

31. The force-limiting and damping device as claimed in claim 1, wherein the limiting module has
   a sleeve element disposed at the bottom side of the connecting segment and located at one side of the mounting segment; and a positioning seat disposed on the tapping segment below the sleeve element at a spaced interval.

32. The force-limiting and damping device as claimed in claim 1, wherein the limiting module has
    a sleeve element disposed at the bottom side of the connecting segment and annularly arranged around an external surface of the mounting segment; and
    a positioning seat disposed on the tapping segment and annularly arranged around the external surface of the mounting segment below the sleeve element at a spaced interval.

33. The force-limiting and damping device as claimed in claim 1, wherein
    the connecting segment has a through slot transversally formed through a sidewall of the connecting segment;
    the mounting segment extends into the through slot via the bottom side of the connecting segment;
    the fixing segment is connected to the mounting segment in the through slot; and
    the force-limiting element is mounted around the mounting segment between the fixing segment and the connecting segment at the through slot.

* * * * *